United States Patent [19]

Holzhauer et al.

[11] Patent Number: 5,728,870
[45] Date of Patent: Mar. 17, 1998

[54] PROCESS FOR PREPARING PURIFIED 2,6-NAPHTHALENEDICARBOXYLIC ACID

[75] Inventors: Juergen K. Holzhauer; Rusins Albertins, both of Naperville; Stephen V. Hoover, Aurora; David L. Sikkenga, Wheaton, all of Ill.

[73] Assignee: Amoco Corporation, Chicago, Ill.

[21] Appl. No.: 726,678

[22] Filed: Oct. 7, 1996

Related U.S. Application Data

[63] Continuation of Ser. No. 206,517, Mar. 4, 1994, Pat. No. 5,563,294, which is a continuation of Ser. No. 65,486, May 19, 1993, abandoned, which is a continuation of Ser. No. 900,637, Jun. 18, 1992, abandoned, which is a continuation-in-part of Ser. No. 810,481, Dec. 19, 1991, abandoned.

[51] Int. Cl.$^6$ .................................................. C07C 51/09
[52] U.S. Cl. .......................... 562/483; 562/485; 562/486; 562/487; 562/488
[58] Field of Search ............................ 562/483, 485, 562/486, 487, 488

[56] References Cited

U.S. PATENT DOCUMENTS

| | | | |
|---|---|---|---|
| 3,671,578 | 6/1972 | Ogata et al. | 260/515 P |
| 4,302,595 | 11/1981 | Schoengen et al. | 562/483 |
| 5,068,410 | 11/1991 | Tanaka et al. | 562/483 |
| 5,149,867 | 9/1992 | Chen et al. | 562/486 |
| 5,256,817 | 10/1993 | Sikkenga et al. | 562/487 |
| 5,563,294 | 10/1996 | Holzhauer et al. | 562/483 |

FOREIGN PATENT DOCUMENTS 0441347  8/1991  European Pat. Off. .

*Primary Examiner*—Jose' G. Dees
*Assistant Examiner*—Rosalynd A. Keys
*Attorney, Agent, or Firm*—Thomas E. Nemo; Wallace L. Oliver

[57] ABSTRACT

A process for preparing purified 2,6-naphthalenedicarboxylic acid which comprises hydrolyzing a dialkyl-2,6-naphthalenedicarboxylate with water at a reaction temperature of at least about 450° F. under liquid phase condition, the amount of water present being sufficient to solubilize, at the reaction temperature, at least about 10 percent of the 2,6-naphthalenedicarboxylic acid formed; and a process for purifying 2,6-naphthalenedicarboxylic acid comprising combining impure 2,6-naphthalenedicarboxylic acid with a purification solvent, heating the resulting mixture under liquid phase conditions at a temperature of at least about 500° F. to form a product mixture and thereafter recovering from the product mixture purified 2,6-naphthalenedicarboxylic acid.

16 Claims, 1 Drawing Sheet ically, this invention relates to an improved process
5,728,870

PROCESS FOR PREPARING PURIFIED 2,6-NAPHTHALENEDICARBOXYLIC ACID

RELATED APPLICATION

This is a continuation of application Ser. No. 08/206,517 filed Mar. 4, 1994 (U.S. Pat. No. 5,563,294); which is a Continuation of Ser. No. 08/065,486, filed May 19, 1993 abandoned; which is a Continuation of Ser. No. 07/900,637, filed Jun. 18, 1992 abandoned; which is a Continuation-in-Part of Ser. No. 07/810,481, filed Dec. 19, 1991 abandoned.

FIELD OF THE INVENTION

This invention relates generally to an improved process for preparing purified 2,6-naphthalenedicarboxylic acid. In one aspect, this invention relates to an improved process for preparing purified 2,6-naphthalenedicarboxylic acid by hydrolyzing a dialkyl-2,6-naphthalenedicarboxylate with water under reaction conditions that provide for large particle size 2,6-naphthalenedicarboxylic acid.

In another aspect, this invention relates to an improved process for purifying 2,6-naphthalenedicarboxylic acid wherein an impure form of 2,6-naphthalenedicarboxylic acid is heated at an elevated temperature in the presence of a solvent for a period of time sufficient to reduce the level of undesirable impurities in the impure 2,6-naphthalenedicarboxylic acid.

BACKGROUND OF THE INVENTION

Dialkyl-2,6-naphthalenedicarboxylates and 2,6-naphthalenedicarboxylic acid are useful monomers for the preparation of high performance polymeric materials. For example, dimethyl-2,6-naphthalenedicarboxylate and 2,6-naphthalenedicarboxylic acid can be reacted with ethylene glycol to prepare poly(ethylene-2,6-naphthalate) (PEN). Fibers and film manufactured from PEN have improved strength and superior thermal properties relative to other polyester materials. Films made from PEN demonstrate, for example, superior resistance to gas diffusion and particularly to the diffusion of carbon dioxide, oxygen and water vapor. Because of its exceptional properties, PEN is especially suitable for applications such as food and beverage containers, particularly for so-called "hot-fill" food and beverage containers, tire cord, magnetic recording tape and electronic components.

Although the dialkyl-2,6-naphthalenedicarboxylates—particularly dimethyl-2,6-naphthalenedicarboxylate—are suitable monomers for preparing PEN and other polymeric materials, in some commericial-scale operations it is preferable to employ 2,6-naphthalenedicarboxylic acid rather than a dialkyl ester. For example, a polyester manufacturer may have equipment and associated processes available for manufacturing polyesters only from an aromatic dicarboxylic acid. In these circumstances, the diester materials would not be suitable and the use of 2,6-naphthalenedicarboxylic acid would be required. Additionally, it is advantageous to use 2,6-naphthalenedicarboxylic acid in the manufacture of polyesters because the condensation of a diacid with a glycol to form a polyester does not form an alcohol by-product as does the condensation of a diester with a glycol. Polyester manufacturers who use diacids such as 2,6-naphthalenedicarboxylic acid do not, therefore, have to provide for the use or sale of the alcohol by-product.

Methods for preparing 2,6-naphthalenedicarboxylic acid include the bromine-promoted, metal-catalyzed, liquid phase oxidation of 2,6-dialkylnaphthalenes. Such processes are disclosed in U.S. Pat. Nos. 3,870,754; 4,950,786 and 4,933,491. The bromine-promoted, metal-catalyzed, liquid phase oxidation of 2,6-dialkylnaphthalenes, particularly 2,6-dimethylnaphthalene, produces a crude product containing a variety of impurities such as brominated 2,6-naphthalenedicarboxylic acids, 2-formyl-6-naphthoic acid, 2-naphthoic acid and trimellitic acid. These impurities, particularly 2-formyl-6-naphthoic acid, are difficult to remove from crude 2,6-naphthalenedicarboxylic acid. The 2,6-naphthalenedicarboxylic acid must, however, be purified before it can be polymerized to form polymeric materials.

The purification of 2,6-naphthalenedicarboxylic acid is considerably more difficult than the purification of a dialkyl-2,6-naphthalenedicarboxytate primarily due to the low solubility of 2,6-naphthalenedicarboxylic acid in most ordinary solvents, and to its high melting point. In the aforementioned U.S. Pat. No. 4,933,491, for example, 2,6-naphthalenedicarboxylic acid was purified only after reacting the 2,6-naphthalenedicarboxylic acid with a lower alkanoic anhydride to produce a component that is soluble in excess alkanoic anhydride. The "solubilized" 2,6-naphthalenedicarboxylic acid was optionally treated with one or more purification procedures. Xu et al. (Chemistry of Synthetic High Polymers, Vol. 10, pp. 107–11, 1984, Chemical Abstracts CA 102: 185547z) describes the purification of 2,6-naphthalenedicarboxylic acid by routine sublimation, recrystallization or distillation as inefficient and difficult due to the poor solubility of 2,6-naphthalenedicarboxylic acid and also because the impurities present, having similar properties; adhere to each other. U.S. Pat. No. 3,649,680 to McNamey discloses a process for purifying aromatic carboxylic adds wherein a mixture of water and an alkanol are added to an impure carboxylic acid paste, the carboxylic acid is separated from the alkanol/water mixture, and the purified carboxylic acid is subsequently washed with water. U.S. Pat. No. 3,671,578 to Ogata discloses a process for preparing 2,6-naphthalenedicarboxylic acid wherein the monoalkali salt of 2,6-naphthalenedicarboxylic acid is heated in water or a water-containing organic solvent, causing disproportionation thereof into 2,6-naphthalenedicarboxylic acid and the dialkali salt of 2,6-naphthalenedicarboxylic acid. U.S. Pat. No. 3,888,921 to Yamamoto et al., discloses a process for purifying 2,6-naphthalenedicarboxylic wherein an aqueous solution of a dialkali salt of crude 2,6-naphthalenedicarboxylic acid is prepared, then 40 to 97 mole percent of the dialkali salt is precipitated as a monoalkali salt while maintaining the pH of the aqueous solution at a value of not lower than 6.3, and converting the precipitate to 2,6-naphthalenedicarboxylic acid. It is disclosed in the Yamamoto et al. patent that the aqueous solution of the dialkali salt of 2,6-naphthalenedicarboxylic acid can be at a temperature of 60° C.–350° C. in the presence of potassium or sodium hydroxide, and it is disclosed that the solution can be treated with a reducing agent such as hydrogen gas, sodium dithionite, lithium aluminum hyddde or sodium borohydride. U.S. Pat. No. 3,781,346 to Norton discloses a process for purifying naphthalene carboxylic acids comprising reacting a solid ammonium salt of the acid with steam at a temperature of from about 200° C. to about 300° C. U.S. Pat. No. 4,794,195 to Hayashi et al. discloses that as it is impossible to purify crude naphthalenedicarboxylic acid to a high purity only by crystallization, and that it is necessary to combine the method of crystallization with other methods such as thermal treatment, oxidative treatment or reductive treatment. However, no specific means for conducting such treatments on 2,6-naphthalenedicarboxylic or other naphthalenedicarboxylic acid is disclosed. USSR Inventor's Certificate No. 486,008, to Kulakov et al. published on Jan. 15, 1976, discloses a method for purifying 2,6-naphthalenedicarboxylic acid by treating impure 2,6-naphthalenedicarboxylic acid having a particle size of 0.05–0.35 mm and containing up to 30% naphthalenemonocarboxylic acid with an aliphatic carboxylic acid at 180°–250° C. This Inventor's Certificate teaches that the 0.05–0.35 mm particle size 2,6-naphthalenedicarboxylic acid is obtained by grinding the 2,6-naphthalenedicarboxylic acid and passing it through a screen with 0.05–0.35 mm holes. Kulakov et al. however, does not teach the preparation of 2,6-naphthalenedicarboxylic acid by the liquid phase oxidation of a 2,6-dialkyl or 2-acryl-6-alkyl naphthalene compound, and the reference does not teach the removal of trimellitic acid from 2,6-naphthalenedicarboxylic acid prepared by such liquid-phase oxidation methods. U.S. Pat. No. 3,584,039 to Meyer discloses a process for preparing fiber-grade terephthalic acid by catalytic hydrogen treatment of dissolved impure terephthalic acid.

In contrast to 2,6-naphthalenedicarboxylic acid, the diesters of 2,6-naphthalenedicarboxylic acid are considerably more soluble than 2,6-naphthalenedicarboxylic acid in ordinary organic solvents such as xylenes and alcohols, and can be purified in the dissolved state. Furthermore, these diesters, particularly the dimethyl ester, are sufficiently volatile so that they can be purified by distillation. Therefore, one potential method for preparing purified 2,6-naphthalenedicarboxylic acid is to convert a purified dialkyl-2,6-naphthalenedicarboxylate to 2,6-naphthalenedicarboxylic acid by reacting the diester with water to hydrolyze the ester bonds and form the free dicarboxylic acid. One such process is disclosed in the aforementioned Xu et al. publication. The process disclosed therein comprises forming purified 2,6-naphthalenedicarboxylic acid by dissolving crude dimethyl-2,6-naphthalenedicarboxylate in a xylene, treating with activated carbon, and then crystallizing purified dimethyl-2,6-naphthalenedicarboxylate. The purified dimethyl-2,6-naphthalenedicarboxylate was subsequently hydrolyzed using a 12% potassium hydroxide solution at reflux conditions, and the solution of hydrolyzed ester was acidified with hydrochloric acid to free purified 2,6-naphthalenedicarboxylic acid. While it is reported that this procedure produces high purity 2,6-naphthalenedicarboxylic acid, the process disclosed would not be desirable for large-scale production. The use of concentrated base to hydrolyze the ester and the required use of an acid to free the salt of 2,6-naphthalenedicarboxylic acid is not economical on a large scale.

Other processes for hydrolyzing dialkyl-2,6-naphthalenedicarboxylates are known. For example, dimethyl-2,6-naphthalenedicarboxylate can be reacted with a molar excess of water in a low temperature, low pressure process, e.g. at 350°–430° F., using an acidic catalyst such as an alkylbenzene sulfonic acid or mineral acid. Such a process produces a 2,6-naphthalenedicarboxylic acid product having a small particle size which is difficult to wash and filter, and that requires large quantities of ethylene glycol to prepare slurries for the manufacture of polyesters such as PEN. Additionally, the hydrolysis reaction is slow under these reaction conditions. In European Patent Application 0432910A, published on Jun. 19, 1991, corresponding to U.S. Pat. No. 5,068,410, a process for hydrolyzing dimethyl-2,6-naphthalenedicarooxylate to 2,6-naphthalenedicarboxylic acid is disclosed wherein an aromatic polycarboxylic acid, for example, pyromellitic acid, trimellitic acid or phthalic acid, is used as a catalyst, it is disclosed therein that these catalysts provide for 2,6-naphthalenedicarboxylic acid with a large particle size, and 2,6-naphthalenedicarboxylic acid having an average particle size as large as 67 microns is described in the examples. It is also taught therein that temperatures in the range of 200°–230° C. may be used and that at temperatures greater than 230° C. the corrosive action of the carboxylic acid is increased and, as a result, corrosion occurs on the surface of the vessel material. The European Patent Application discloses that the concentration of aromatic polycarboxylic acid catalyst may be in the range of 0.2–20% by weight, however, all of the examples in the application utilize an amount of aromatic polycarboxylic acid catalyst that is from 15 to 100 weight percent of the dimethyl-2,6-naphthalenedicarboxylate that is hydrolyzed. In European Patent Application 441347A, a process for hydrolyzing a dialkylester of a naphthalenedicarboxylic acid is disclosed wherein the dialkylester is reacted, in the presence of an esterification catalyst, within a temperature range of 70°–350° C. and in a solvent inclusive of a monocarboxylic acid containing no unsaturated bond group and having a carbon number of 1–10. It is also disclosed that the solvent contains water in addition to the monocarboxylic acid.

All of the aforementioned processes for hydrolyzing dimethyl-2,6-naphthalenedicarboxylate require long reaction times and/or the presence of a catalyst or carboxylic acid solvent to carry out the hydrolysis. The art, therefore, needs an improved process for preparing 2,6-naphthalenedicarboxylic acid from a dialkyl-2,6-naphthalenedicarboxylate, and the present invention provides such an improved process.

Consequently, in one aspect of the present invention, a dialkyl-2,6-naphthalenedicarboxylate is hydrolyzed with water at a temperature of at least about 450° F. and the amount of water present is sufficient to solubilize at least about 10% of the 2,6-naphthalenedicarboxylic acid formed. Under these conditions, the hydrolysis of the dialkyl-2,6-naphthalenedicarboxylate is rapid and, particularly when the temperature of the process is about 500° F. or greater, the product 2,6-naphthalenedicarboxylic acid is in the form of large particles having an average size of about 100 microns or greater thereby making the product highly suitable for filtering, washing and preparing PEN. An advantage of the instant invention is that other materials, such as acidic acid catalysts or monocarboxylic acid solvents, need not be added to the hydrolysis mixture and, consequently, need not be separated from the final product as in the prior art processes. Extra processing steps are therefore eliminated. Additionally, when the hydrolysis process of the instant invention is carried out such that a major portion of the 2,6-naphthalenedicarboxylic acid product is dissolved in the hydrolysis water, the 2,6-naphthalenedicarboxylic acid produced is in the form of large, well-formed crystals that are superior for forming low viscosity slurries of 2,6-naphthalenedicarboxylic acid in ethylene glycol. These slurries are used for preparing PEN.

Processes for hydrolyzing dimethylterephthalate to terephthalic acid are also known. U.S. Pat. No. 3,594,414 to Katzschmann discloses a process for preparing fiber-grade terephthalic acid comprising hydrolyzing dimethylterephthalate at a temperature of from about 180° to 280° C., preferably 200°–250° C., and preferably in the presence of neutral salts such as sodium chloride, potassium chloride and calcium chloride. In U.S. Pat. No. 4,302,595 to Schoengen et al., a process is disclosed for preparing fiber-grade terephthalic acid from intermediate stage crude dimethylterephthalate wherein in one step of the process the crude dimethylterephthalate, having a limited content of intermediate oxidation products, is hydrolyzed in water in at least two stages at a temperature between 140° C. and 350° C., preferably from 240° to 280° C., in the first stage, and 180° to 220° C. in the second stage to produce a reaction mixture containing terephthalic acid. Although a hydrolysis temperature of up to 350° C. is disclosed in the Schoengen et al. patent, the examples provided therein use a temperature of 250° C., and it is taught that hydrolysis temperatures above 300° C. do not ensure economical operation.

In another aspect of the present invention, 2,6-naphthalenedicarboxylic acid is purified without requiring its conversion to a diester. Thus, a purified form of 2,6-naphthalenedicarboxylic acid is produced directly and it can be used to manufacture, for example, polyester materials, or such purification process can be used as a preliminary purification before the 2,6-naphthalenedicarboxylic acid is converted to a dialkyl ester. The use of higher purity 2,6-naphthalenedicarboxylic acid in the preparation of a dialkylester provides for a higher quality dialkyl-2,6-naphthalenedicarboxylate.

The processes of this invention can produce 2,6-naphthalenedicarboxylic acid having a mean particle size of greater than 100 microns, and even greater than 200 microns. Large particle size 2,6-naphthalenedicarboxylic acid is advantageous because it provides for more efficient filtration and washing procedures when the 2,6-naphthalenedicarboxylic acid and is being purified. Additionally, the 2,6-naphthalenedicarboxylic acid produced by the processes of this invention have very low levels of "fine" particles that tend to plug filters and other apparatus used for conducting solid-liquid separations.

SUMMARY OF THE INVENTION

A process for preparing purified 2,6-naphthalenedicarboxylic acid comprises (a) hydrolyzing a dialkyl-2,6-naphthalenedicarboxylate with water at a reaction temperature of at least about 450° F. under liquid phase conditions and for a time sufficient to convert a major portion of the dialkyl-2,6-naphthalenedicarboxylate to 2,6-naphthalenedicarboxylic acid thereby forming a reaction product mixture, the amount of water present being sufficient to solubilize, at the reaction temperature, at least about 10 weight percent of the 2,6-naphthalenedicarboxylic acid formed; and (b) recovering 2,6-naphthalenedicarboxylic acid from the reaction product mixture. This process is hereinafter referred to as "hydrolysis process." Additionally, although one or more hydrolysis catalysts can be added to the hydrolysis process, the instant hydrolysis process proceeds at high reaction rates in the absence of an added hydrolysis catalyst or co-solvent such as a monocarboxylic acid.

The instant invention is also a process for purifying 2,6-naphthalenedicarboxylic acid comprising combining impure 2,6-naphthalenedicarboxylic acid with a purification solvent, heating the resulting mixture under liquid phase conditions at a temperature of at least about 500° F. to form a product mixture, and thereafter recovering from the product mixture purified 2,6-naphthalenedicarboxylic acid. This purification process wherein the 2,6-naphthalenedicarboxylic acid is heated with a solvent at an elevated temperature is hereinafter referred to as the "high temperature process" and it can be used to reduce substantially the levels of undesirable impurities such as the brominated 2,6-naphthalenedicarboxylic acids, trimellitic acid and 2-formyl-6-naphthoic acid in the 2,6-naphthalenedicarboxylic acid. Both processes produce 2,6-naphthalenedicarboxylic acid in the form of large particles which are desirable for filtering and washing operations, and for preparing polyesters such as PEN.

DETAILED DESCRIPTION OF THE INVENTION

Figure 1:
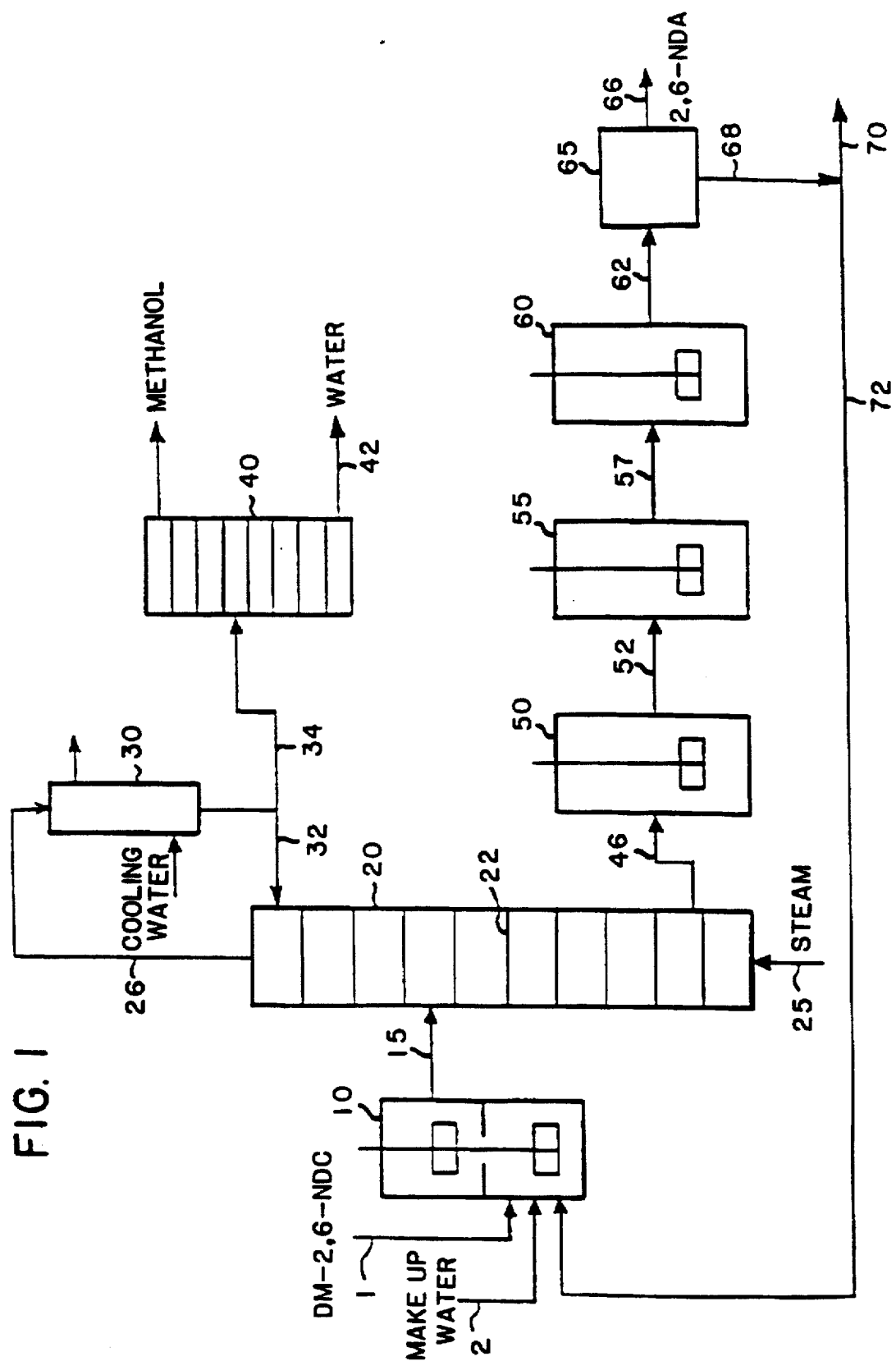
FIG. 1 is a schematic diagram of a preferred method for operating the hydrolysis process of this invention in the continuous mode.

In the hydrolysis process of this invention a dialkyl-2,6-naphthalenedicarboxylate is reacted with water under liquid phase conditions at an elevated temperature of at least about 450° F. to hydrolyze the dialkyl ester and form 2,6-naphthalenedicarboxylic acid. When a pure dialkyl-2,6-naphthalenedicarboxylate is used, purified 2,6-naphthalenedicarboxylic acid is produced.

The dialkyl-2,6-naphthalenedicarboxylate hydrolyzed is preferably a lower dialkyl ester, wherein the alkyl portion of the ester groups contains from 1 to about 4 carbon atoms. For example, dimethyl-, diethyl-, di-n-propyl-, diisopropyl, di-n-butyl-, ethylmethyl- and diisobutyl-2,6-napthalenedicarboxylate are suitable dialkyl-2,6-naphthalenedicarboxylates. Dimethyl-2,6-naphthalenedicarboxylate, however, is the most preferred dialkyl-2,6-naphthalenedicarboxylate because it is most easily prepared and purified. The dialkyl-2,6-naphthalenedicarboxylates can be prepared by any known method. For example, they can be prepared by the method disclosed in U.S. Pat. No. 4,886,901 to Holzhauer et al. wherein a naphthalenedicarboxylic acid is esterified with methanol and then purified by recrystallization, and they can be prepared by the methods disclosed in U.S. Pat. No. 4,847,400 to Steinmetz et al. The dialkyl-2,6-naphthalenedicarboxylates used in the hydrolysis process of this invention can conveniently be prepared by esterifying 2,6-naphthalenedicarboxylic acid prepared by the liquid-phase, cobalt, manganese and bromine catalyzed oxidation of a 2,6-dialkylnaphthalene. Preferably, the 2,6-dialkylnaphthalene is 2,6-dimethylnaphthalene. A suitable method for oxidizing 2,6-dimethylnaphthalene to 2,6-naphthalenedicarboxylic acid is disclosed in Albertins et al., U.S. Pat. No. 4,933,491.

Before the dialkyl-2,6-naphthalenedicarboxylate is used in the hydrolysis process of this invention, it is preferably purified to a purity of at least about 95%, preferably at least about 99% and most preferably at least about 99.5% by one or more suitable methods of purification such as recrystallization, distillation, adsorption, sublimation, etc. The combination of recrystallizing dimethyl-2,6-naphthalenedicarboxylate from a solvent such as methanol or xylene, followed by a fractional distillation of the recrystallized dimethyl-2,6-naphthalenedicarboxylate, is a particularly suitable method for preparing pure dimethyl-2,6-naphthalenedicarboxylate.

The reaction temperature for the hydrolysis of the dialkyl-2,6-naphthalenedicarboxylate is at least about 450° F., preferably at least about 500° F., and most preferably at least about 570° F. At these reaction temperatures, the hydrolysis reaction proceeds rapidly and, as will be described in greater detail hereinbelow, these reaction temperatures provide for the formation of 2,6-naphthalenedicarboxylic acid having a large particle size making the manipulation of these particles, for example, in washing and filtering procedures easier. A maximum hydrolysis temperature is preferably about 700° F.

The pressure for the hydrolysis reaction is a pressure sufficient to maintain a major portion, preferably at least about 75 percent, and more preferably at least about 95 percent of the water in the liquid phase. Suitable reaction pressures are in the range of about 20 atmospheres to about 200 atmospheres.

The amount of water used in the hydrolysis reaction is related to the temperature at which the hydrolysis reaction is conducted. Water should be present in the reaction mixture in an amount sufficient to solubilize, at the reaction temperature, at least about 10 weight percent, preferably at least about 25 weight percent, more preferably at least about 50 weight percent of the 2,6-naphthalenedicarboxylic acid produced in the hydrolysis reaction. Most preferably, the amount of water present in the reaction mixture is an amount sufficient to solubilize all of the 2,6-naphthalenedicarboxylic acid produced in the hydrolysis reaction. We have determined that the hydrolysis reaction proceeds rapidly when the aforementioned amounts of water are present, and, moreover, the 2,6-naphthalenedicarboxylic acid produced under these reaction conditions has an average (mean) particle size of at least about 100 microns. The amount of water necessary to achieve the hereinabove solubility levels can be determined from the solubility data presented in Example 11. For example, at a reaction temperature of 608° F., the solubility of 2,6-naphthalenedicarboxylic acid is reported in Example 11 as 33.2 grams per 100 grams of water. Therefore, assuming substantially complete hydrolysis of a sample of dimethyl-2,6-naphthalenedicarboxylate, and if it is desired to operate under reaction conditions where substantially all of the 2,6-naphthalenedicarboxylic acid is solubilized, the weight ratio of water to dimethyl-2,6-naphthalenedicarboxylate charged to the hydrolysis reaction mixture should be at least approximately 2.7:1, respectively. This is because each gram of dimethyl-2,6-naphthalenedicarboxylate produces, after complete hydrolysis, approximately 0.885 gram of 2,6-naphthalenedicarboxylic acid and, based on the solubility data in Example 11, approximately 2.7 grams of water are required to solubilize 0.885 gram of 2,6-naphthalenedicarboxylic acid at 608° F. This calculation does not take into consideration the amount of water consumed in the reaction; therefore, additional water can be added. Also, this calculation provides the minimum amount of water required to achieve complete solubility. A similar calculation at 500° F., and assuming 10 percent of the 2,6-naphthalenedicarboxylic acid will be solubilized, results in a value of 3.3 grams of water for each gram of dimethyl-2,6-naphthalenedicarboxylate charged to the hydrolysis reaction. This value also does not take into consideration the consumption of water by the hydrolysis reaction. Therefore, additional water should be added, i.e. at least two moles of water per mole of dialkyl-2,6-naphthalenedicarboxylate charged to the reaction mixture.

These calculations for determining the amount of water charged to the hydrolysis reaction mixture assume that the water contains no other component to affect the solubility of 2,6-naphthalenedioarboxylic acid. Therefore, if other components are added, the solubility data provided in Example 11 may not apply. Also, if the herein disclosed hydrolysis process is practiced wherein water is recycled, the recycled water may contain, depending on the temperature at which the 2,6-naphthalenedicarboxylic acid is partitioned from the water (i.e. mother liquor), various amounts of 2,6-naphthalenedicarboxylic acid. This 2,6-naphthalenedicarboxylic acid should be counted, after adjusting for molecular weight differences, as part of the charge of dialkyl-2,6-naphthalenedicarboxylate for the purpose of determining the level of water charged to the reaction mixture. Therefore, when the water charged to the hydrolysis reaction already contains, for example, dissolved 2,6-naphthalenedicarboxylic acid, the amount of water charged to the hydrolysis reaction should be an amount sufficient to solubilize at least about 10 weight percent, preferably at least about 25 weight percent, more preferably at least about 50 weight percent, and most preferably all of the 2,6-naphthalenedicarboxylic acid in the reaction product mixture.

While the solubility data in Example 11 can be used to determine the amount of water required to achieve the desired dissolution of 2,6-naphthalenedicarboxylic acid in the hydrolysis reaction mixture, it is generally preferable when hydrolyzing the preferred dimethyl-2,6-naphthalenedicarboxylate to use a weight ratio of water to dimethyl-2,6-naphthalenedicarboxylate of at least about 4:1, and preferably at least about 5:1, respectively. The preferred reaction temperature being at least about 500° F., preferably at least about 540° F., and most preferably at least about 570° F. At these conditions, the hydrolysis rate is rapid and large particle size 2,6-naphthalenedicarboxylic acid is formed. Preferably, the maximum hydrolysis temperature is about 700° F. and, preferably the maximum weight ratio of water to dimethyl-2,6-naphthalenedicarooxylate is about 25:1, more preferably about 10:1, respectively.

It is advantageous to conduct the hydrolysis reaction so that substantially all of the dialkyl-2,6-naphthalenedicarboxylate charged to the reaction mixture is converted to 2,6-naphthalenedicarboxylic acid, thereby eliminating a step to separate the desired 2,6-naphthalenedicarboxylic acid from unreacted diester. However, the hydrolysis reaction can be conducted at lower conversion such as, for example, 50 percent conversion of the dialkyl-2,6-naphthalenedicarboxylate. Therefore, the hydrolysis reaction should be conducted for a time sufficient to convert at least 50 percent of the dialkyl-2,6-naphthalenedicarboxylate, more preferably at least about 95 percent and, as stated above, most preferably for a time sufficient to convert substantially all of the dialkyl-2,6-naphthalenedicarboxylate to 2,6-naphthalenedicarboxylic acid.

When operating the hydrolysis process of this invention under conditions where at least 10 percent and, preferably, where substantially all of the 2,6-naphthalenedicarboxylic acid is solubilized during the reaction, 2,6-naphthalenedicarboxylic acid can be produced having excellent particle size, for example an average particle size of at least about 100 microns and preferably at least about 200 microns as measured by a Microtrac™ particle analyzer. Preferably, the average particle size is up to about 1000 microns, more preferably up to about 800 microns. The 2,6-naphthalenedicarboxylic acid produced by the hydrolysis process also has a very low amount of "fines". For example, less than about 5 weight percent of the 2,6-naphthalenedicarboxylic acid particles are less than 11 microns, preferably less than about 2 weight percent of the particles are less than about 11 microns, as measured by a Microtrac™ particle analyzer. Furthermore, the 2,6-naphthalenedicarboxylic acid prepared using conditions where substantially all of the acid is solubilized has, in addition, excellent crystal morphology in that the particles are well-defined, individual crystals that are substantially non-porous rather than highly porous aggregates of small crystals. These large, well-formed, well-defined crystals are desirable for forming slurries with, for example, ethylene glycol because the large, well-defined, individual crystals that are substantially non-porous do not require a large quantity of a slurry medium such as ethylene glycol to form an easily mixed and easily pumped slurry of 2,6-naphthalenedicarboxylic acid. More specifically, in a continuous process for preparing PEN, it is desirable to add 2,6-naphthalenedicarboxylic acid to the polymerization reactor as a pumpable slurry of 2,6-naphthalenedicarboxylic acid in ethylene glycol. Furthermore, since the mole ratio of ethylene glycol to 2,6-naphthalenedicarboxylic acid in PEN is 1:1, it is desirable to charge to the polymerization reactor a mole ratio of ethylene glycol to 2,6-naphthalenedicarboxylic acid as close to 1:1 as possible. This is because any excess glycol must be removed in a later stripping step, and excess glycol also leads to the formation of undesirable ethers which can become incorporated into the polyester. The 2,6-naphthalenedicarboxylic acid prepared by the process of this invention wherein a major portion of the 2,6-naphthalenedicarboxylic acid produced in the hydrolysis reaction was solubilized required about 2–3 times less ethylene glycol to achieve the same viscosity of a slurry of ethylene glycol and 2,6-naphthalenedicarboxylic acid wherein the 2,6-naphthalenedicarboxylic acid was prepared by a hydrolysis process conducted at 380°–400° F. using p-toluenesulfonic acid as a catalyst and a 5:1 ratio of water to dimethyl-2,6-naphthalenedicarboxylate. At a reaction temperature of 380°–400° F. and a weight ratio of water to dimethyl-2,6-naphthalenedicarboxylate of 5:1, only approximately 1.4 weight percent of the 2,6-naphthalenedicarboxylic acid is solubilized. The particles produced by the low-temperature process have a highly porous structure and require larger amounts of ethylene glycol to form a pumpable slurry. Under microscopic examination they appear as an agglomeration of very small crystals. This structure causes the high porosity. European Patent Application WO 90/14375 discloses methods for preparing PEN.

Operating under hydrolysis reaction conditions wherein substantially all of the 2,6-naphthalenedicarboxylic acid produced is solubilized is also advantageous, particularly when using a baffled, plug flow-type reactor or other type of baffled reactor, because plugging problems are eliminated. Whereas, when operating under conditions where a portion of the 2,6-naphthalenedicarboxylic acid is not in solution, the resulting slurry of 2,6-naphthalenedicarboxylic acid in the reactor and piping could lead to plugging.

During the hydrolysis reaction of the dialkyl-2,6-naphthalenedicarboxylate, it is preferable to remove a portion of the alcohol as it is formed. Removal of the alcohol provides for more rapid and more complete conversion of the dialkyl-2,6-naphthalenedicarboxylate to 2,6-naphthalenedicarboxylic acid. The alcohol can be removed from the reaction mixture by, for example, venting a portion of the gaseous phase of the reaction mixture. However, unless provisions are taken to separate the alcohol from the water, this venting procedure will also remove a quantity of water. Depending on the amount of water initially used, this may be a loss of water significant enough to affect the rate of hydrolysis or the dissolution of 2,6-naphthalenedicarboxylic acid. However, any water lost can optionally be replaced. It is advantageous to remove, during the hydrolysis reaction, at least about 30 weight percent of the alcohol, more preferably at least about 90 percent and most preferably at least about 99% of the theoretical amount of alcohol produced by the hydrolysis reaction.

Following the hydrolysis reaction, the reaction mixture is optionally cooled to crystallize the 2,6-naphthalenedicarboxylic acid. When operating under conditions where substantially all of the 2,6-naphthalenedicarboxylic acid is in solution, this cooling step is necessary to recover the 2,6-naphthalenedicarboxylic acid by crystallizing the dissolved 2,6-naphthalenedicarboxylic acid. Preferably, the reaction mixture is cooled to a temperature below about 400° F., more preferably below about 250° F. The rate of cooling affects particle size of the 2,6-naphthalenedicarboxylic acid produced. It is preferable to cool the reaction mixture at a rate that promotes the formation of large particle size 2,6-naphthalenedicarboxylic acid. Cooling rates of less than about 50° F. per minute, preferably less than about 40° F. per minute and most preferably less than about 10° F. per minute provide for large particle size 2,6-naphthalenedicarboxylic acid.

Following the optional cooling step, the 2,6-naphthalenedicarboxylic acid is recovered by partitioning the 2,6-naphthalenedicarboxylic acid from residual water using a suitable means for partitioning a solid phase component from a liquid phase component. For example, solid 2,6-naphthalenedicarboxylic acid can be partitioned from the water phase by filtration, centrifugation, settling, and the like. In this partitioning or separation process the large particle size 2,6-naphthalenedicarboxylic acid produced by the process of this invention is advantageous in that large particles do not "blind" filters and plug centrifuge baskets as readily as fine particles, or retain as much mother liquor, thereby making the partitioning process considerably more efficient. It is desirable to partition the 2,6-naphthalenedicarboxylic acid from the water at an elevated temperature, preferably at a temperature of at least about 150° F., and more preferably at a temperature of at least about 200° F. Filtration at these temperatures provides for a purer 2,6-naphthalenedicarboxylic acid.

After the 2,6-naphthalenedicarboxylic acid is partitioned from the water, it is preferably washed with a suitable solvent such as water, a low molecular weight carboxylic acid, e.g. acetic acid, or an aromatic hydrocarbon such as toluene, xylene, etc. Water is the preferred solvent for washing the 2,6-naphthalenedicarboxylic acid. A suitable amount of solvent to wash the 2,6-naphthalenedicarboxylic acid is an amount such that the weight ratio of solvent to 2,6-naphthalenedicarboxylic acid is at least about 1:1, and preferably at least about 2:1, respectively. it is also preferable to conduct the washing step at an elevated temperature. For example, when water is the solvent for the washing step, it is advantageous for the water to be at a temperature of at least about 150° F. Preferably the water should be at a temperature in the range of about 200° F. to about 300° F. Due to the solubility of 2,6-naphthalenedicarboxylic acid in water, the amount of water used to wash the 2,6-naphthalenedicarboxylic acid preferably should not be an amount that will dissolve more than about 10 weight percent of the 2,6-naphthalenedicarboxylic acid being washed. Otherwise, the losses of 2,6-naphthalenedicarboxylic acid will be too great.

The hydrolysis process of this invention can be conducted in the batch mode, semi-continuous mode or in the continuous mode. In the batch mode, all of the reactants are charged to a suitable reaction zone at the start of the reaction. As described hereinabove, a portion of the reaction vapor can be released from the reaction zone to further the conversion of the dialkyl-2,6-naphthalenedicarboxylate to 2,6-naphthalenedicarboxylic acid. In the semi-continuous mode of operation, at least one of the reactants is added to the reaction zone during the course of the reaction. For example, a quantity of water can be charged to the reaction zone initially and the dialkyl-2,6-naphthalenedicarboxylate can be added to the reaction zone during the course of the reaction. In the continuous mode of operation, the reactants are added to the reaction zone continuously throughout the course of the reaction and the reaction product mixture is continuously removed from the reaction zone. For commercial-scale operations, it is preferable to operate in the continuous mode. The reaction zone used for a continuous mode of operation can be any suitable reaction apparatus such as at least one continuous stirred tank reactor, a plug flow reactor, a column reactor or a combination of such reactors. The liquid phase reaction residence time, depending on the preselected reaction temperature and ratio of dialkyl-2,6-naphthalenedicarboxylate to water, is suitably about 1 min. to about 5 hrs., preferably about 1 min. to about 2 hours.

A preferred method for conducting the hydrolysis process of this invention in a continuous manner is to use a reactor that is essentially a distillation column equipped with a means for providing liquid hold-up in the column. Suitable means for providing the liquid hold-up include, for example, trays, highly structured packing, and the like. In this method, a dialkyl-2,6-naphthalenedicarboxylate and, optionally, water are introduced near or at the top of the column and an inert gas or, preferably, steam is added to the bottom of the reactor. The addition of steam at the bottom of the reactor is required if water is not added with the dialkyl-2,6-naphthalenedicarboxylate. The steam or inert gas introduced at the bottom of the column reactor provides for the removal of alcohol from the reaction mixture thereby helping to drive the equilibrium controlled reaction to completion. An aqueous solution or slurry of purified 2,6-naphthalenedicarboxylic acid is withdrawn at or near the bottom of the column reactor. This solution or slurry is directed to a crystallization zone, followed by a zone for separating the crystallized 2,6-naphthalenedicarboxylic acid from the water.

Preferably, the vapor exiting the top of the column reactor, which vapor comprises a mixture of alcohol and water, is condensed. Part of the condensate is returned to the top of the column reactor and the remaining part is directed to a means for separating the alcohol from the water, e.g. a distillation column. The feed mixture of dialkyl-2,6-naphthalenedicarboxylate and water (if added) is preferably added to the column reactor at a feed location somewhat below the top of the column. The portion of the column above the feed location will preclude mono-alkyl-2,6-naphthalenedicarboxylate and dialkyl-2,6-naphthalenedicarboxylate from entering and, potentially, fouling the overhead condenser. This column reactor, particularly with the inert gas or steam stripping, provides for a very efficient hydrolysis reaction because alcohol is rapidly separated from the reaction mixture thereby shifting the equilibrium to the desired dicarboxylic acid product.

Before the dialkyl-2,6-naphthalenedicarboxylate is fed to the column reactor, the dialkyl-2,6-naphthalenedicarboxylate can be "prereacted" with water in a prereactor, such as, for example, one or more stirred tank reactors. This prereaction converts the dialkyl-2,6-naphthalenedicarboxylate into a mixture of 2,6-naphthalenedicarboxylic acid and mono-alkyl-2,6-naphthalenedicarboxylic acid. Introducing such a mixture into the column reactor will preclude the presence of a liquid dialkyl-2,6-naphthalenedicarboxylate phase in the column reactor. The melting point of dimethyl-2,6-naphthalenedicarooxylate, for example, is about 374° F. (190° C.) and, therefore, any dimethyl-2,6-naphthalene dicarboxylate that is present in the reactor will exist as a separate liquid phase. The presence of two liquid phases in the column reactor is not desirable because the contents of the column reactor are not mechanically agitated, although such agitation could be provided, if required, by a suitable agitating means. A suitable liquid phase residence time in the column reactor is about 1 min. to about 5 hours. The reaction temperature and water levels in the column reactor are the same as those described hereinabove for the hydrolysis reaction. In order to preclude plugging the column reactor, it is most preferable to operate the reaction under conditions wherein all or substantially all of the 2,6-naphthalenedicarboxylic acid is in solution. Additionally, complete solubilization provides for the largest 2,6-naphthalenedicarboxylic acid particles and 2,6-naphthalenedicarboxylic acid in the form of well-formed, substantially individual crystals having substantially no internal porosity.

FIG. 1 represents, in schematic form, the preferred method for conducting the continuous hydrolysis of a dialkyl-2,6-naphthalenedicarboxylate to form purified 2,6-naphthalenedicarboxylic acid. For the purposes of this description, dimethyl-2,6-naphthalenedicarboxylate is the diester that is hydrolyzed. The reaction temperatures and quantity of water in the prereactor and column reactor, as well as the crystallization and filtration temperatures, are as described hereinabove.

Referring to FIG. 1, dimethyl-2,6-naphthalenedicarboxylate, preferably in molten form, is added to prereactor 10 along with water using feed lines 1 and 2, respectively. The liquid-phase residence time of the reaction mixture in reactor 10 is preferably sufficient to convert most of the dimethyl-2,6-naphthalenedicarboxylate to a mixture of 2,6-naphthalenedicarboxylic acid and mono-methyl-2,6-naphthalenedicarboxylic acid. Prereactor 10 comprises a stirred tank reactor having a lower and upper section separated by a baffle. The reaction mixture exits from the upper section of prereactor 10 through line 15 and is directed to the upper part of column reactor 20. Column reactor 20 comprises a vertical column equipped with a plurality of trays 22 to provide liquid holdup in the column. Steam is added to the bottom of column 20 through steam line 25. Overhead vapor is removed from column reactor 20 and is directed through line 26 to condenser 30. Condensate from condenser 30 is partitioned and part of the condensate is returned to column 20 through line 32 and part is directed through line 34 to distillation column 40 where methanol is separated from water. The water is recycled to prereactor 10 through line 42, and the methanol is directed to, for example, an esterification reactor (not shown) for converting 2,6-naphthalenedicarboxylic acid to dimethyl-2,6-naphthalenedicarboxylate. The hydrolysis reaction product, preferably having all the 2,6-naphthalenedicarboxylic acid dissolved in the reaction mixture, exits column reactor 20 through line 46 located near the bottom of column. The reaction mixture passes through a series of stirred tank vessels 50, 55 and 60 where the reaction mixture is cooled to slowly crystallize the 2,6-naphthalenedicarboxylic acid. Cooling can be accomplished by lowering the pressure and allowing the reaction mixture to cool by evaporative cooling. Vessels 50, 55 and 60 can be substituted with one or more batch crystallizers or with a-substantially plug flow-type crystallizer. Product slurry exits last crystallizer 60 through line 62 and is directed to centrifuge 65 wherein the product 2,6-naphthalenedicarboxylic acid is separated from mother liquor. Product exits the centrifuge through line 66 and is typically sent to a dryer (not shown). Mother liquor is removed from centrifuge through line 68 and is recycled through line 72 to prereactor 10. Part of the mother liquor is purged through line 70.

An advantage of the present hydrolysis reaction of this invention is that the hydrolysis reaction is rapid and large particle size 2,6-naphthalenedicarboxylic acid is produced without the inclusion of a hydrolysis catalyst or other component such as a monocarboxylic acid co-solvent in the reaction mixture. Consequently, this invention is the hereinabove described hydrolysis reaction carried out in the substantial absence and, preferably, in the absence of a hydrolysis catalyst and/or monocarboxylic acid co-solvent. However, if desired, a hydrolysis catalyst can be added to the hydrolysis reaction mixture. For example, from about 0.001 to about 2.0 weight percent of a catalyst, based on the weight of the dialkyl-2,6-naphthalenedicarboxylate charged to the hydrolysis reaction, can be used. Suitable catalysts include, for example, strong acids such as hydrochloric acid and sulfuric acid; alkyl or aryl sulfonic acids, such as toluene sulfonic acid; or one or more metal-based catalysts, such as, for example, an oxide, halide, sulfate or carboxylic acid salt of antimony, copper, zinc, etc.

This invention is also 2,6-naphthalenedicarboxylic acid produced by the hydrolysis process described herein, particularly when the hydrolysis reaction is conducted at temperatures of at least about 500° F., and more preferably at temperatures of at least about 540° F., and most preferably at temperatures of at least about 570° F. The 2,6-naphthalenedicarooxylic acid produced by the hydrolysis process of this invention is characterized by its large particle size wherein the average particle size, as measured by a Microtrac™ particle size analyzer, is at least about 100 microns and preferably at least about 200 microns. Preferably, the average particle size is up to about 1000 microns, more preferably up to about 800 microns. The 2,6-naphthalenedicarboxylic acid produced by the hydrolysis process of this invention also contains less than about 5 weight percent 2,6-naphthalenedicarboxylic acid particles having a particle size less than 11 microns, more preferably less than about 2 weight percent.

As described hereinabove, a second aspect of this invention comprises a process for purifying 2,6-naphthalenedicarboxylic acid by contacting impure 2,6-naphthalenedicarboxylic acid with a purification solvent at an elevated temperature for a time sufficient to reduce the level of undesirable impurities in the impure 2,6-naphthalenedicarboxylic acid. In this high temperature process an impure form of 2,6-naphthalenedicarboxylic acid is combined with a suitable purification solvent and the resulting mixture is heated under liquid phase conditions at a temperature of at least about 500° F. to form a product mixture. Purified 2,6-naphthalenedicarboxylic acid is thereafter recovered from the product mixture. It has been found, unexpectedly, that such high temperature process converts trimellitic acid to other materials such as for example o-phthalic acid, terephthalic acid and isophthalic acid. The high temperature provides for purer 2,6-naphthalenedicarboxylic acid, and because such phthalic acids do not complex as strongly as trimellitic acid to oxidation catalyst metals such as cobalt and manganese, process streams remaining after the high temperature treatment can be recycled to an oxidation reactor with reduced levels of trimellitic acid. In addition to reducing the levels of trimellitic acid in impure 2,6-napthalenedicarboxylic acid, the herein disclosed high temperature process also reduces the level of other undesirable impurities such as 2-formyl-6-naphthoic acid and the bromo-2,6-naphthalenedicarboxylic acids.

The 2,6-naphthalenedicarboxylic acid used in the high temperature process of this invention can be obtained from any source. A preferred source of 2,6-naphthalenedicarboxylic acid, however, is 2,6-naphthalenedicarboxylic acid prepared by the liquid phase, metal-catalyzed oxidation of a 2,6-dialkyl or 2-acyl-6-alkyl naphthalene such as, for example, 2,6-dimethylnaphthalene, 2-methyl-6-acetylnaphthalene, 2-methyl-6-butrylnaphthalene, 2,6-diethylnaphthalene, 2,6-diisopropylnaphthalene, and the like. Methods for conducting the liquid phase, heavy-metal catalyzed oxidation of an alkyl- or acyl-substituted aromatic compound such as the naphthalene compounds described hereinabove, to the corresponding aromatic carboxylic acid are well known in the art. For example, U.S. Pat. Nos. 4,950,786; 4,933,491; 3,870,754 and 2,833,816 disclose such oxidation methods. In general, suitable heavy-metal oxidation catalysts include those metals having an atomic number of about 21 to about 82, inclusive. The preferred oxidation solvent is a low molecular weight monocarboxylic acid having 2 to about 6 carbon atoms, inclusive, preferably it is acetic acid or mixtures of acetic acid and water. A reaction temperature of about 300° F. to about 450° F. is typical, as the reaction pressure is such that the reaction mixture is under liquid phase conditions. A promoter such as a low molecular weight ketone having 2 to about 6 carbon atoms or a low molecular weight aldehyde having 1 to about 6 carbon atoms can also be used. Bromine promoter compounds known in the art such as hydrogen bromide, molecular bromine, sodium bromide and the like can also be used. A source of molecular oxygen is also required, and typically it is air.

A particularly suitable method for oxidizing 2,6-dialkyl and 2-acyl-6-alkylnaphthalenes, and particularly 2,6-dimethylnaphthalene, to 2,6-naphthalenedicarboxylic acid is disclosed in U.S. Pat. No. 4,933,491 to Albertins et al. Suitable solvents for such liquid phase oxidation reaction include benzoic acid, any aliphatic $C_2$–$C_6$ monocarboxylic acid such as acetic acid, propionic acid, n-butyric acid, isobutyric acid, n-valeric acid, trimethylacetic acid, caproic acid, and water. Preferably the solvent is a mixture of water and acetic acid, which mixture is preferably 1 to 20 weight percent water. The source of molecular oxygen employed in such liquid phase oxidation can vary in molecular oxygen content from that of air to oxygen gas. Because of economy, air is the preferred source of molecular oxygen.

The catalyst employed in such oxidation of a 2,6-dialkyl or 2-acyl-6-alkylnaphthalene comprises a bromine-containing compound and at least one of a cobalt- and manganese-containing compound. Preferably, the catalyst comprises cobalt-, manganese-, and bromine-containing components. The ratio of cobalt (calculated as elemental cobalt) in the cobalt component of the catalyst to 2,6-dimethylnaphthalene in the liquid phase oxidation is in the range of about 0.1 to about 100 milligram atoms (toga) per gram mole of 2,6-dimethylnaphthalene. The ratio of manganese (calculated as elemental manganese) in the manganese component of the catalyst to cobalt (calculated as elemental cobalt) in the cobalt component of the catalyst in the liquid-phase oxidation is in the range of from about 0.1 to about 10 mga per mga of cobalt. The ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.1 to about 1.5 mga per mga of total cobalt and manganese. Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1.0 to 1.5:1.0 bromine-to-total cobalt and manganese milligram atom ratio is provided by a suitable bromine source such as elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzylbromide, tetrabromoethane, ethylenedibromide, etc.). The total bromine in molecular bromine and ionic bromide is used to determine satisfaction of the elemental bromine-to-total cobalt and manganese milligram atom ratio of 0.1:1.0 to 1.5:1.0. The bromine ion released from the organic bromides at the oxidation operating conditions can be readily determined by known analytical means. Tetrabromoethane, for example, at operating temperatures of 335° F. to 440° F. has been found to yield about 3 effective gram atoms of bromine per gram mole.

In operation, the minimum pressure at which the oxidation reactor is maintained is that pressure which will maintain a substantial liquid phase of the 2,6-dialkyl or 2-acyl-6-alkylnaphthalene and at least 70 weight percent of the solvent. The 2,6-dialkyl or 2-acyl-6-alkylnaphthalene and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 $kg/cm^2$ to about 35 $kg/cm^2$, and typically are in the range of from about 10 $kg/cm^2$ to about 30 $kg/cm^2$. The temperature range within the oxidation reactor is generally from about 250° F., preferably from about 350° F. to about 450° F., preferably to about 420° F. The solvent residence time in the oxidation reactor is generally from about 20 to about 150 minutes and preferably from about 30 to about 120 minutes.

Such oxidation can be performed either in a batch, continuous, or semicontinuous mode. In the batch mode, the naphthalene compound, solvent and the catalyst components are initially introduced batchwise into the reactor, and the temperature and pressure of the reactor contents are then raised to the desired levels for the commencement of the oxidation reaction. Air is introduced continuously into the reactor. After commencement of the oxidation reaction, for example, after all of the 2,6-dialkyl or 2-acyl-6-alkylnaphthalene has been completely introduced into the reactor, the temperature of the reactor contents is raised. In the continuous mode, each of the naphthalene compound, air, solvent, and catalyst are continuously introduced into the reactor, and a product stream comprising 2,6-naphthalenedicarboxylic acid and catalyst components dissolved in the solvent is withdrawn from the reactor. In the semicontinuous mode, the solvent and catalyst are initially introduced into the reactor and then the 2,6-dialkyl or 2-acyl-6-alkylnaphthalene and air are continuously introduced into the reactor. For large-scale commercial operation it is preferable to use a continuous oxidation process. In such a process wherein 2,6-dimethylnaphthalene is oxidized, the weight ratio of monocarboxylic acid solvent to 2,6-dimethylnaphthalene is preferably about 2:1 to about 12:1, the mga ratio of manganese to cobalt is about 5:1 to about 0.3:1, the mga ratio of bromine to the total of cobalt and manganese is about 0.3:1 to about 0.8:1, and the total of cobalt and manganese, calculated as elemental cobalt and elemental manganese is at least about 0.40 weight percent based on the weight of the solvent, and the oxidation reaction temperature is about 370° F. to about 420° F. Acetic acid is the most suitable solvent for such preferred continuous oxidation of 2,6-dimethylnaphthalene.

After an oxidation reaction is completed, the oxidation product mixture can be heated to a high temperature, e.g. 500° F. to 700° F., to reduce undesirable impurities contained in the oxidation reaction mixture. Such high temperature heat treatment can be conducted with or without the presence of hydrogen gas and a noble metal hydrogenation catalyst.

Subsequent to the oxidation reaction and optional high temperature treatment, the oxidation reaction mixture is typically cooled to promote the crystallization of the 2,6-naphthalenedicarboxylic acid from the reaction mixture; and the 2,6-naphthalenedicarboxylic acid is partitioned (i.e., separated) from the oxidation reaction mixture by any suitable means for separating a solid from a liquid phase. For example, by centrifugation, filtration and the like. The separated 2,6-naphthalenedicarboxylic acid is typically washed with one or more solvents either at ambient or, preferably, an elevated temperature. Most suitably the wash solvent is water, acetic acid or other low molecular weight aliphatic carboxylic acid or mixtures of water and a low molecular weight carboxylic acid. The 2,6-naphthalenedicarboxylic acid isolated from such an oxidation method contains impurities and by-products such as trimellitic acid and, if a bromine compound is used as a promoter during the liquid phase, brominated naphthalenedicarboxylic acids. Other impurities include 2-formyl-6-naphthoic acid from the incomplete oxidation of the alkyl group and, typically, the metal catalysts used for the liquid-phase oxidation. Such 2,6-naphthalenedicarboxylic acid typically contains up to about 3 wt. % brominated-2,6-naphthalenedicarboxylic acid, 1 wt. % 2-formyl-6-naphthoic acid and 5 wt. % trimellitic acid. The high temperature process of this invention can be used to purify such impure 2,6-naphthalenedicarboxylic acid.

Purification solvents that are suitable for the high temperature process of this invention include any solvent that will at least partially dissolve 2,6-naphthalenedicarboxylic acid at an elevated temperature and which solvent does not react with 2,6-naphthalenedicarboxylic acid and which does not decompose at an elevated temperature used for this process so as to produce impurities. For example, solvents having reactive groups such as amines, alcohols, phenols and thiols are generally not suitable as solvents. Suitable solvents, however, include water, low molecular weight carboxylic acids and mixtures of water and low molecular weight carboxylic acids. Preferably, such low molecular weight carboxylic acids have about 1 to about 8 carbon atoms and are preferably monocarboxylic acids. Preferably, the low molecular weight carboxylic acids are saturated in that they do not contain any carbon-carbon multiple bonds. Examples of suitable low molecular weight carboxylic acids solvents include acetic acid, propionic acid, iso- and n-butylic acid, benzoic acid, fluoro-, bromo-, chloroacetic acid, and the like. Acetic and propionic acid are most preferred. Due to availability and cost, and also because it is the acid primarily used in the hereinabove described liquid-phase, metal-catalyzed oxidation reaction, acetic acid in the most preferred low molecular weight carboxylic acid solvent for the high temperature process of this invention. When mixtures of water and a low molecular weight carboxylic acid are employed in the high temperature process of this invention, the weight ratio of water to carboxylic acid solvent can range from about 1:99 to about 99:1, respectively, preferably about 2:98 to about 98:2, respectively. A preferred solvent is a mixture of water and low molecular weight carboxylic acid, preferably acetic acid, wherein the amount of acid present is about 5 to about 20 wt. % based on the total weight of the solvent. This mixture facilitates the removal of oxidation catalyst metals. Additionally, when water or a mixture of water and low molecular weight carboxylic acid is used, it is advantageous to include a small amount, for example 0.01 to about 10 wt. % of a strong acid such as hydrochloric acid, sulfuric acid, hydrobromic acid, trifluoroacetic acid and the like. These strong acids also facilitate the removal of oxidation catalyst metals from the 2,6-naphthalenedicarboxylic acid.

In the present high temperature process, the amount of purification solvent used in the reaction is an amount sufficient to dissolve, at the reaction temperature, at least a portion of the 2,6-naphthalenedicarboxylic acid charged to the reaction mixture. Preferably, the amount of solvent used is an amount that will dissolve a major portion and more preferably substantially all of the 2,6-naphthalenedicarboxylic acid charged to the reaction mixture. However, purification of impure 2,6-naphthalenedicarboxylic acid occurs when at least 10 weight percent, more preferably at least 20 weight percent of the 2,6-naphthalenedicarboxylic acid is in solution under the reaction conditions for the high temperature process. The weight ratio of solvent to 2,6-naphthalenedicarboxylic acid is suitably at least about 1:1, more preferably at least about 2:1, and most preferably at least about 2.5:1; respectively. Typically, the weight ratio of solvent to 2,6-naphthalenedicarboxylic acid is no more than about 10:1, respectively.

Reaction temperature is a critical feature of the high temperature process of the present invention. We have found, unexpectedly, that the high temperature treatment of impure 2,6-naphthalenedicarboxylic acid containing impurities such as trimellitic acid, 2-formyl-6-naphthoic acid and bromo-2,6-naphthalanedicarboxylic acid causes a decrease in the levels of these impurities. The decrease is not simply the separation of the impurity from the impure 2,6-naphthalenedicarboxylic acid, as might be expected from a normal recrystallization process, but is due to the conversion of the impurities to other compounds. The result is that a purer 2,6-naphthalenedicarboxylic acid can be produced and, significantly, the process streams remaining after removal of the 2,6-naphthalenedicarboxylic acid have a reduced level of trimellitic acid, making them more suitable for recycle to an oxidation reaction mixture.

The reaction temperature for the high temperature purification process of this invention is suitably at least about 500° F., more preferably at least about 550° F., and most preferably at least about 600° F. The period of time at which the reaction mixture is maintained at these temperatures is a period sufficient to reduce the level of impurities in the 2,6-naphthalenedicarboxylic acid charged to the reaction mixture by conversion to other compounds. Such time period can range from about 0.1 minute to several hours, depending on the temperature selected, the level of impurities present in the impure 2,6-naphthalenedicarboxylic acid, and the degree of purity desired. The combination of temperature and reaction time should preferably be sufficient to reduce the level of trimellitic acid present in the reaction mixture by at least about 40 percent, more preferably by at least about 60 percent. For most purposes, the reaction time period will be at least about 1 minute, preferably at least about 5 minutes. The temperature for the high temperature process is preferably no greater than about 700° F. Above 700° F. excessive decomposition of 2,6-naphthalenedicarboxylic acid may occur.

If the purification solvent selected has a low vapor pressure at the temperature selected for the high temperature purification process, it will be necessary to conduct the reaction in a pressure vessel in order to maintain solvent in the liquid state. Consequently, the pressure for the high temperature process should be sufficient to maintain liquid phase conditions, and preferably wherein at least about 50 weight percent of the solvent in the reaction mixture is in the liquid state. For example, when the preferred solvents are used, i.e. solvents such as water, low molecular weight carboxylic acids, and mixtures of water and low-molecular weight carboxylic acids, the pressure for the reaction is up to about 3000 psig, more preferably 2000 psig. Preferably, the pressure is at least about 200 psig.

Following the high temperature treatment, the reaction product mixture is subject to a separation process wherein the purified 2,6-naphthalenedicarboxylic acid formed in the high temperature process is separated from the solvent used. Any means for separating a solid from a liquid is suitable for this separation step. For example, filtration (vacuum, atmospheric, or at elevated pressures) settling and centrifugation can be employed. Combinations of these separation procedures can also be used. It is also preferable to wash the purified 2,6-naphthalenedicarboxylic acid with a solvent after it is separated from the solvent used for the high temperature process. This washing step further purifies the 2,6-naphthalenedicarboxylic acid by removing residual solvent used for the high temperature purification process. The residual solvent typically contains undesirable impurities. Most preferably, the solvent used to wash the 2,6-naphthalenedicarboxylic acid is the same solvent used for the high temperature treatment. The wash solvent can also contain from about 0.01 to about 10 wt. % of one or more strong acids such as hydrochloric acid, sulfuric acid, hydrobromic acid, trifluoroacetic acid, and the like. The amount of solvent used to wash the 2,6-naphthalenedicarboxylic acid is an amount sufficient to remove at least a major portion of the solvent remaining from the high temperature process. Preferably, the weight ratio of wash solvent to 2,6-naphthalenedicarboxylic acid is at least about 0.2:1, more preferably at least about 0.4:1, and most preferably at least about 0.8:1, respectively. The washing can be completed in any suitable manner, however it is preferable to simply add the washing solvent to the 2,6-naphthalenedicarboxylic acid while the 2,6-naphthalenedicarboxylic acid is still in the apparatus used to separate the 2,6-naphthalenedicarboxylic acid from the reaction mixture solvent. For example, when a centrifuge is used to separate the 2,6-naphthalenedicarboxylic acid from the reaction mixture solvent, washing can be completed by adding the washing solvent to the centrifuge cake while the cake is still on the centrifuge basket. Alternatively, the 2,6-naphthalenedicarboxylic acid can be washed by slurrying the 2,6-naphthalenedicarboxylic acid in the wash solvent followed by a second separation step wherein the wash solvent is separated from the 2,6-naphthalenedicarboxylic acid. Two or more washing steps can be used. Most preferably, the washing solvent should be at an elevated temperature, for example, a temperature from about 100° F. to about 400° F.

Prior to separating the purified 2,6-naphthalenedicarboxylic acid from the reaction mixture formed in the high temperature process, the reaction mixture can be cooled to promote crystallization of the 2,6-naphthalenedicarboxylic acid. However, as expected, cooling will cause not only the crystallization of the desired 2,6-naphthalenedicarboxylic acid but will also cause the precipitation or crystallization of undesired impurities. Consequently, a suitable temperature for separating the 2,6-naphthalenedicarboxylic acid from the reaction mixture solvent is a temperature that provides the desired purity of 2,6-naphthalenedicarboxylic acid and the desired recovery of 2,6-naphthalenedicarboxylic acid. For example, the reaction mixture can De cooled to a temperature that is about 20° F. to about 400° F., more preferably about 200° F. to about 350° F. below the reaction temperature, before the 2,6-naphthalenedicarboxylic acid is separated from the reaction mixture. Most preferably, the reaction mixture is cooled to a temperature in the range of about 100° F. to about 400° F. before the 2,6-naphthalenedicarboxylic acid is separated therefrom. Additionally, it is desirable to cool the reaction mixture slowly. Slower cooling of the reaction mixture provides for 2,6-naphthalenedicarboxylic acid having a larger average (mean) particle size, and 2,6-naphthalenedicarboxylic acid having a lower percentage of very small particle size 2,6-naphthalenedicarboxylic acid. The large particle size 2,6-naphthalenedicarboxylic acid allows for a more efficient separation process when 2,6-naphthalenedicarboxylic acid is separated from the reaction mixture solvent because the larger particles do not plug or "blind" filter plates or centrifuge baskets when filtration and/or centrifugation is used for the separation process. Also, as discussed, hereinabove, large particle size 2,6-naphthalenedicarboxylic acid is desirable for making PEN. The rate of cooling the reaction mixture is preferably no greater than about 50° F. per minute, more preferably no more than about 40° F. per minute, and most preferably no more than about 10° F. per minute. When operating this process in a continuous mode, a scraped-surface tubular heat exchanger can be used to obtain low cooling rates. By using the high temperature process of this invention, 2,6-naphthalenedicarboxylic acid having a mean particle size, as measured by a Microtrac™ particle analyzer, of at least 100 microns can be obtained. Additionally, 2,6-naphthalenedicarboxylic acid having a mean particle size of at least about 200 microns has been prepared. Additionally, the 2,6-naphthalenedicarboxylic acid prepared by the high temperature process of this invention has very low levels of fines, for example, less than 5 weight percent of the 2,6-naphthalenedicarboxylic acid is of a particle size less than 11 microns, preferably less than about 2 weight percent.

In one embodiment of the high temperature process, an inert atmosphere is used during the heating step. For example, a gas such as nitrogen, helium or argon or mixture of one or more thereof is added to the reactor vessel to eliminate or reduce the amount of oxygen that would otherwise be present due to the presence of air.

In another embodiment of the present high temperature process, the reaction mixture containing the 2,6-naphthalenedicarboxylic acid can be treated with hydrogen in the presence of one or more hydrogenation catalysts. The treatment provides for an even greater reduction of impurities such as 2-formyl-6-naphthoic acid in the impure 2,6-naphthalenedicarboxylic acid feed. Additionally, the use of hydrogen facilitates the removal of the bromo-2,6-naphthalenedicarboxylic acids and converts the bromo-2,6-naphthalenedicarboxylic acid to 2,6-naphthalenedicarboxylic acid. When using hydrogen, the preferred solvents include water and mixtures of water and low molecular weight carboxylic acids such as acetic acid. Mixtures of low molecular weight carboxylic acids are also suitable. Acetic acid is the most preferred low molecular weight carboxylic acid. The amount of water can range from about 1 to about 99 wt. %. Preferably, the amount of water is about 2 to about 98 wt. %. A highly preferred solvent is a mixture of water and acetic acid wherein the water is present in an amount of about 5 wt. % to about 95 wt. %, more preferably 15 wt. % to about 85 wt. %. When using hydrogen, the amount of solvent preferably should be an amount that substantially completely dissolves the 2,6-naphthalenedicarboxylic acid at the temperature used for the purification method.

When hydrogen is used, the hydrogen is typically hydrogen gas at a partial pressure typically of from about 1 to 1000 psig, and preferably 5–300 psig. An inert gas, such as nitrogen, helium or argon, can be used with the hydrogen gas. The hydrogenation catalyst can be any hydrogenation catalyst that will catalyze the reaction of hydrogen with impurities and provide for the elimination of the 2-formyl-6-naphthoic acid and/or bromo-2,6-naphthalenedicarboxylic acids in the impure 2,6-naphthalenedicarboxylic acid. The preferred hydrogenation catalysts are the members of the Group VIII noble metals that include platinum, palladium, rhodium, ruthenium, osmium, iridium and mixtures thereof. Platinum, palladium and ruthenium are particularly effective hydrogenation catalysts for the method of this invention. The aforementioned Group VIII metals can be used in a form supported on a suitable support material, or they can be used in an unsupported form. Support materials such as alumina, silica-alumina, silica, titania, clays, zirconia, etc. can be used. Supports made from carbon and/or charcoal are highly suitable. The amount of one or more of the aforementioned Group VIII metals on the support; preferably carbon and/or charcoal, is about 0.1 wt. % to about 5.0 wt. %, based on the weight of the catalyst. The amount of catalyst used is a function of variables such as reaction temperature, concentration of impurities in the naphthalenedicarboxylic acid and the reaction residence time. However, in general, the weight ratio of impure naphthalenedicarboxylic acid to active component of the hydrogenation catalyst is about 200:1 to about 30,000:1, more preferably 2000:1 to about 20,000:1. Highly preferred catalysts are 0.03–1.0 wt. % palladium on a high surface area carbon support and 0.03–1.0 wt. % ruthenium on a high surface area carbon support. Such catalysts are available from Engelhard Corp., Edison, N.J.; Degussa Corp., South Plainfield, N.Y.; and Aldrich Chemical Co., Milwaukee, Wis.

When using hydrogen, the reaction time necessary to achieve acceptable purification of the 2,6-naphthalenedicarboxylic acid will vary depending on the amount of hydrogenation catalyst used, the concentration of hydrogen and the temperature. However, in general, the reaction residence or the weight hourly space velocity of the reaction mixture in contact with the hydrogenation catalyst is from about 200 to 200,000 grams of reaction solution per gram of active component of the hydrogenation catalyst, per hour. More preferably, this value is about 1,000 to about 100,000.

After the treatment of the reaction mixture with hydrogen, the reaction mixture is separated from the hydrogenation catalyst. If a continuous process is used wherein the reaction mixture is passed over or through a fixed bed of hydrogenation catalyst, this separation step is not necessary. However, if the hydrogenation catalyst is dispersed in the reaction mixture such as in a batch-type reaction where the hydrogenation catalyst is simply added to the reaction mixture in for example, a granular form, the hydrogenation catalyst must be separated from the reaction mixture by one or more means such as filtration, settling or centrifugation. When the catalyst is used in such dispersed form, it is desirable to use conditions wherein the 2,6-naphthalenedicarboxylic acid is substantially and, more preferably, completely dissolved in the reaction solvent thereby facilitating the separation of the reaction mixture from the hydrogenation catalyst. However, when operating under reaction conditions wherein the 2,6-naphthalenedicarboxylic acid is not all in solution, the hydrogenation catalyst can be contained on one side of a screen or filter or other barrier that permits the passage of dissolved 2,6-naphthalenedicarboxylic acid, dissolved impurities and hydrogen gas, but does not permit the passage of undissolved or particulate material such as insoluble impurities and 2,6-naphthalenedicarboxylic acid not in solution. Using this type of arrangement, the hydrogenation reaction can proceed without subjecting the hydrogenation catalyst to insoluble components that could deactivate the hydrogenation catalyst.

In another embodiment of the high temperature process, particularly when the solvent is water or mixtures of water and a low molecular weight carboxylic acid, activated carbon can be added to further improve the purity of the resulting 2,6-naphthalenedicarboxylic acid. The use of activated carbon is most suitable under conditions where the 2,6-naphthalenedicarboxylic acid is essentially completely in solution during the high temperature treatment. A hot filtration of the mixture containing the activated carbon separates the carbon from the reaction mixture, and subsequent cooling provides for the crystallization of purified 2,6-naphthalenedicarboxylic acid. The weight ratio of activated carbon to impure 2,6-naphthalenedicarboxylic acid is suitably about 0.005:1 to about 0.06:1, more preferably about 0.01:1 to about 0.03:1.

Furthermore, the high temperature process of this invention for purifying 2,6-naphthalenedicarboxylic acid does not require the formation and use of soluble mono- and/or dialkali metal salts, or other soluble salts, or soluble esters or anhydrides, as required for prior processes. The impure 2,6-naphthalenedicarboxylic charged to the purification process and the 2,6-naphthalenedicarboxylic acid present during the purification process is preferably mostly in the protonated acid form, i.e., where the carboxylate groups are in the protonated or hydrogen form, and more preferably where at least about 90 mole percent of the naphthalenedicarboxylic acid is in the protonated form, and most preferably wherein substantially all of the naphthalenedicarboxylic acid is in the protonated or hydrogen form rather than a salt, ester, anhydride or other derivative.

It should also be understood that the high temperature process of this invention is a process separate from the liquid-phase oxidation process wherein a 2,6-dialkyl- or 2,6-alkylacyl-substituted naphthalene feed compound is oxidized to 2,6-naphthalenedicarobxylic acid. The high temperature process of this invention is most preferably used to purify 2,6-naphthalenedicarboxylic acid made by such liquid-phase, metal-catalyzed oxidation of a 2,6-dialkyl- or 2,6-alkylacyl-substituted naphthalene compound, for example, 2,6-dimethylnaphthalene.

In addition to the hereinabove described processes, this invention is 2,6-naphthalenedicarboxylic acid having a mean particle size of at least about 100 microns, preferably at least about 175 microns, more preferably at least about 200 microns, and preferably up to about 1000 microns, more preferably up to about 800 microns, preferably wherein such 2,6-naphthalenedicarboxylic acid contains less than 5 percent of the particles having a particle size under 11 microns, preferably less than 2 percent of the particles having a particle size under 11 microns, additionally, such 2,6-naphthalenedicarboxylic acid is preferably at least 95% pure by weight, more preferably at least 98% pure by weight. This invention also includes the compositions comprising a physical mixture of 2,6-naphthalenedicarboxylic acid having an average, particle size of at least about 100 microns, preferably at least about 125 microns, and preferably up to about 1000 microns, more preferably up to about 800 microns, and a glycol containing 2 to about 6 carbon atoms, and preferably ethylene glycol, wherein the mole ratio of glycol to 2,6-naphthalenedicarboxylic acid is about 1:1 to about 10:1, preferably 1:1 to about 4:1, respectively.

This invention is also 2,6-naphthalenedicarboxylic acid having a mean particle size of at least about 100 microns, preferably at least about 200 microns, and preferably up to about 1000 microns, more preferably up to about 800 microns, wherein the 2,6-naphthalenedicarboxylic acid is at least about 95% pure by weight, more preferably at least about 98% pure by weight, and wherein such 2,6-naphthalenedicarboxylic acid particles are in the form of well-formed crystals having substantially no internal porosity and which, therefore, do not require large amounts of ethylene glycol or other glycol such as 1,4-dihydroxybutane to form a pumpable slurry; and this invention includes physical mixtures of such 2,6-naphthalenedicarboxylic acid with a glycol containing 2 to about 6 carbon atoms, preferably ethylene glycol, wherein the mole ratio of glycol to 2,6-naphthlenedicarboxylic acid is about 1:1 to about 10:1, and preferably 1:1 to about 4:1, respectively.

Furthermore, this invention is a composition consisting essentially of a physical mixture of 2,6-naphthalenedicarboxylic acid and a glycol wherein the composition has a Brookfield viscosity of no more than about 1000 centipoise measured using a number 4 spindle rotated at 50 rpm, and wherein the molar ratio of glycol to 2,6-naphthalenedicarboxylic acid is about 1:1 to about 4:1, preferably about 2:1 to about 4:1, respectively. The glycol contains 2 to about 6 carbon atoms, most preferably the glycol is ethylene glycol. This invention is also a composition consisting essentially of a physical mixture of 2,6-naphthalenedicarboxylic acid and a glycol wherein the Brookfield viscosity of the composition (number 4 spindle, 50 rpm) is no more than about 3000 centipoise and the mole ratio of glycol, preferably ethylene glycol, to 2,6-naphthalenedicarboxylic acid is about 1:1 to about 3.5:1, preferably about 2:1 to about 3.5:1, respectively.

The following examples demonstrate the processes of this invention. These examples also demonstrate the hereinabove described compositions. In these examples, dimethyl-2,6-naphthalenedicarboxylate is referred to as DM-2,6-NDC, the mono-methyl ester of 2,6-naphthalenedicarboxylic acid is MM-2,6-NDC, 2,6-naphthalenedicarboxylic acid is 2,6-NDA, 2-naphthoic acid is 2-NA, 2-formyl-6-naphthoic acid is 2-FNA, bromo-2,6-naphthalenedicarboxylic acids are Br-2,6-NDA, trimellitic acid is TMLA, terephthalic acid is TA, isophthalic acid is IA and dimethyl ether is DME. The DM-2,6-NDC used for these examples was obtained by esterifying the 2,6-NDA formed by the liquid phase oxidation of 2,6-dimethylnaphthalene using cobalt, manganese and bromine as the oxidation catalyst. The DM-2,6-NDC was esterified and purified according to the procedure disclosed in U.S. Pat. No. 4,886,901 to Holzhauer et al. The organic components were analyzed by liquid chromatography; the metal analyses were conducted by Inductively Coupled Plasma (ICP) analysis or by x-ray fluorescence spectroscopy. ND or values reported as 0.00 means not detected.

Color of the 2,6-naphthalenedicarboxylic acid was evaluated visually as noted, and it was evaluated by its optical density (OD) at 380 nm. Optical density at 380 nm is the absorbance of a 0.5% (weight/volume) solution in a 50 mm pathlength cell. A Perkin-Elmer 552A UV-Vis spectrophotometer (or similar instrument) can be used. In this procedure, after calibrating the spectrophotometer at 380 nm with the reference and sample cells containing 4.0N $NH_4OH$, the sample cell of the spectrophotometer is filled with a solution prepared by dissolving 0.25 grams of 2,6-naphthalenedicarboxylic acid in 50.0 ml of 4.0N $NH_4OH$. The absorbance at 380 nm (read within one hour of sample preparation) is the OD at 380 nm.

The color of the 2,6-naphthalenedicarboxylic acid was also evaluated by Tri-stimulus Color measurements, L, a* and b*. The measurement of the b*value of a solid on the Hunter Color Scale is described in Hunter, *The Measurement of Appearance*, Chapter 8, pp. 102–132, John Wiley & Sons, N.Y., N.Y. (1975), and in Wyszecki et al., *Color Science, Concepts and Methods, Quantitative Data and Formulae*, 2d Ed., pp. 166–168, John Wiley & Sons, N.Y., N.Y. (1982).

More specifically, the b*-value of purified 2,6-naphthalenedicarboxylic acid was determined using a Diano Match Scan Spectrophotometer as follows. 2,6-Naphthalenedicarboxylic acid was pressed into a pellet by placing 7 grams of 2,6-naphthalenedicarboxylic acid into a 32 mm mold and applying 7000 psi pressure for at least 90 seconds. The pellet was then irradiated with white light that was UV-filtered. The spectrum of the visible light reflected from the sample was determined and Tri-stimulus values (X, Y, and Z) were computed using the CIE Standard Observer functions. Using the weighted-ordinate method, Tri-stimulus values are obtained from the following equations:

$$X = \sum_{400}^{700} R_\lambda \bar{x}_\lambda, \quad Y = \sum_{400}^{700} R_\lambda \bar{y}_\lambda, \quad Z = \sum_{400}^{700} R_\lambda \bar{z}_\lambda,$$

where $R_\lambda$ is the percent reflectance of the object at wavelength $\lambda$ and $\bar{x}_\lambda$, and $\bar{y}_\lambda$, and $\bar{z}_{80}$ are the Standard Observer functions at wavelength $\lambda$ for CIE Illuminant D65. The Tri-stimulus values, X, Y and Z, identify the color of the object in terms of the mixture of the primary lights that match it visually. Tri-stimulus values, however, are of limited use as color specifications because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts Tri-stimulus values to L*, a*, and b* values as shown below:

$$L^* = 25(100Y/Y_o)^{1/3} - 16$$

$$a^* = 500[(X/X_o)^{1/3} - (Y/Y_o)^{1/3}]$$

$$b^* = 200[(Y/Y_o)^{1/3} - (Z/Z_o)^{1/3}]$$

The L*-value is a measure of the luminosity or whiteness of an object where L*=100 is pure white, L*=0 is black, and in between is gray. The L*-value is strictly a function of the Tri-stimulus Y-value. The b*-value is a measure of the yellowness-blueness attribute where positive b*-values represent yellow appearance and negative b*-values represent blue appearance. The b*-value is a function of both Tri-stimulus values Y and Z.

Particle size was measured using a Microtrac II™ Standard Range Analyzer manufactured by Leeds and Northrup Co., St. Petersburg, Fla. Methanol (or water) was used as circulating liquid for suspending the 2,6-naphthalenedicarboxylic acid particles. This method is based on laser light scattering, and provides both a mean (average) and median value for the particles measured as well as the percent of the particles having a particle size less than 11 microns.

It is to be understood that the following examples are being provided to set forth embodiments of the present invention and are not intended to limit the scope thereof.

U.S. patent application Ser. No. 07/810,481 filed on Dec. 19, 1991 is hereby specifically incorporated by reference.

EXAMPLE 1

Comparative

Dimethyl-2,6-naphthalenedicarboxylate was hydrolyzed in the batch mode using a 3.33:1 weight ratio of distilled water to dimethyl-2,6-naphthalenedicarboxylate using p-toluenesulfonic acid as a catalyst. A stirred, 6-gallon pressure vessel constructed of 316 stainless steel was used for the hydrolysis. The reaction times, pressure, temperature and analysis of the resulting 2,6-naphthalenedicarboxylic acid are provided in Table 1. In each of Runs 1 and 2, as noted, the product from an initial four hour reaction was reacted a second time under identical conditions for an additional four hours using fresh water and a fresh catalyst charge. 1950 Grams of dimethyl-2,6-naphthalenedicarboxylate were charged to the reactor. After filtration at room temperature, the 2,6-NDA product was washed with about 1200 grams of water.

The solubility of 2,6-naphthalenedicarboxylic acid in water at 430° F. (220° C.) is approximately 0.5/100 g (See Example 11). Therefore, at these reaction conditions, assuming 100% conversion to 2,6-naphthalenedicarboxylic acid, it is calculated that only about 1.9 weight percent of the 2,6-naphthalenedicarboxylic acid product was in solution at the end of the hydrolysis reaction. As the data in Table 1 show, the 2,6-naphthalenedicarboxylic acid produced had a median particle size of about 6.8 microns.

TABLE 1

|  | Run 1 | Run 2 |
|---|---|---|
| Solvent Ratio[a] | 3.33:1 | 3.33:1 |
| Wt. % p-TSA[b] | 0.78 | 0.78 |
| Reaction Temp., °F. | 430 | 430 |
| Reaction Press., psig | 350 | 350 |
| Reaction Time, hrs | 4 + 4 | 4 + 4 |
| Product Analysis |  |  |
| Visual Color | White | White |
| OD (at 380 nm) | 0.025 | 0.035 |
| Median Particle Size, (Microns) | 6.8 | 6.7 |
| Mean Particle Size (Microns) | 11.5 | 6.8 |
| Wt. % DM-2,6-NDC | ND | 0.04 |
| Wt. % MM-2,6-NDC | 0.17 | 0.21 |
| Metal Analysis[c] ppm |  |  |
| Al | 2.0 | 1.9 |
| Cr | 1.6 | 1.6 |
| Fe | 3.1 | 3.0 |

[a]Weight ratio of water to DM-2,6-NDC.
[b]Weight percent of p-toluene sulfonic acid based on DM-2,6-NDC.
[c]Only for metals at greater than 1 ppm.

EXAMPLE 2

Dimethyl-2,6-naphthalenedicarboxylate was hydrolyzed at elevated temperatures and elevated pressures in the batch-mode in a stirred, 300 ml Hastelloy C autoclave reactor. 37.5 Grams of dimethyl-2,6-naphthalenedicarboxylate were charged to the reactor. No catalyst was used. The 2,6-NDA product was separated from the mother liquor by filtration at room temperature followed by washing with about 150 grams of water. The reaction time, temperature, pressure and analysis of the resulting 2,6-naphthalenedicarboxylic acid are provided in Table 2. During each of the runs reported in Table 2, approximately one-half of the solvent was unintentionally lost. This loss of solvent likely caused the removal of methanol from the reaction mixture thereby shifting the equilibrium towards 2,6-naphthalenedicarboxylic acid. Runs 1, 2 and 3 reported in Table 2 were run consecutively in the same autoclave reactor.

These data demonstrate that the hydrolysis reaction is rapid at temperatures of 540° F. and greater in the absence of a catalyst. A product containing only about 0.144 wt. % MM-2,6-NDC was obtained which result is superior to that using the two-stage reaction reported in Table 1. Additionally, the particle size of the 2,6-naphthalenedicarboxylic acid produced by this process is approximately 4 to 7 times larger than the 2,6-naphthalenedicarboxylic acid produced by the low-temperature hydrolysis reported in Table 1.

The metals in the product 2,6-naphthalenedicarboxylic acid are due either to corrosion of the Hastelloy C autoclave or, more likely, to contaminants from previous uses of the autoclave reactor. However, as shown by Example 6, Run 2, which used a much larger reactor and, consequently, a much smaller ratio of reactor surface to reaction mixture, metal contamination was not observed to a significant extent in the product. The color data reported in Table 2 show that the product is gray-colored, however, the OD measurements, which are measured using a filtered solution of the 2,6-NDA in aqueous base, are quite low at 0.015–0.025, indicating that the color-causing impurities are most likely inorganic contaminants.

Based on the data from Example 11, the solubility of 2,6-naphthalenedicarboxylic acid in water at 540° F. is approximately 6.6 g/100 g. Therefore, at the reaction conditions shown for Run 2, assuming 100% conversion to 2,6-naphthalenedicarboxylic acid, it is calculated that 30 weight percent of the 2,6-naphthalenedicarboxylic acid product was solubilized. At 590° F., the solubility of 2,6-naphthalenedicarboxylic acid in water is 22.7 g/100 g. Therefore, the reaction conditions for Runs 1 and 3, assuming approximately 100% conversion to 2,6-naphthalenedicarboxylic acid, it is calculated that approximately all of the product acid was solubilized throughout the hydrolysis reaction. Since it was not possible to tell when the solvent was lost during these runs, the effect of the loss of solvent on the particle size cannot be determined. Nevertheless, exceptionally large particle size 2,6-naphthalenedicarboxylic acid was formed by this process as shown by the particle size data.

TABLE 2

|  | Run 1 | Run 2 | Run 3 |
|---|---|---|---|
| Solvent Ratio[a] | 4:1 | 4:1 | 4:1 |
| Catalyst | None | None | None |
| Reaction Temp., °F. | 590 | 540 | 590 |
| Reaction Press., psig | 1370 | 920 | 1530 |
| Reaction Time, hrs. | 1.0 | 1.0 | 0.17 |

TABLE 2-continued

|  | Run 1 | Run 2 | Run 3 |
|---|---|---|---|
| Product Analysis |  |  |  |
| Visual Color | Gray | Gray | Gray |
| OD (380 nm) | 0.020 | 0.015 | 0.025 |
| Median Particle Size (Microns) | 30.1 | 116.9 | 110.3 |
| Mean Particle Size (Microns) | 34.4 | 142.9 | 130.7 |
| Wt. % Particles <11 microns | 13.0 | 2.3 | 1.7 |
| Wt. % DM-2,6-NDC | <0.032 | 0.061 | 0.446 |
| Wt. % MM-2,6-NDC | 0.144 | 1.20 | 6.76 |
| Metal Analysis,[b] ppm |  |  |  |
| Al | 8.9 | 6.0 | 4.8 |
| Ca | 2.3 | 3.6 | 2.0 |
| Co | 21.9 | 13.6 | 1.31 |
| Cr | 39.5 | 19.9 | 11.4 |
| Cu |  | 1.9 |  |
| Fe | 123 | 48 | 7.3 |
| K | 1.8 |  |  |
| Mg |  | 12.6 | 4.3 |
| Mn | 1.02 | 3.19 | 1.3 |
| Mo | 21.2 | 15.9 | 15.7 |
| Na |  | 1.7 |  |
| Ni | 83 | 25.3 | 7.6 |
| Ti | 1.53 |  |  |
| Zn |  | 1.8 |  |

[a]Weight ratio of water to DM-2,6-NDC
[b]Only for metals at greater than 1 ppm.

EXAMPLE 3

Dimethyl-2,6-naphthalenedicarboxylate was hydrolyzed in the batch-mode using a 1 liter titanium pressure reactor in the absence of a catalyst. 115.5 Grams of dimethyl-2,6-naphthalenedicarboxylate were charged to the reactor. Product was separated from mother liquor by filtration at room temperature followed by washing with about 450 grams of water. The reaction time, reaction temperature, reaction pressure and analysis of the resulting 2,6-naphthalenedicarboxylic acid are provided in Table 3. Runs 1–3 in Table 1 were run consecutively in the same titanium reactor.

These data show the rapid hydrolysis of dimethyl-2,6-naphthalenedicarboxylate at about 540° F. and 590° F. in the absence of a catalyst. Additionally, these data show that the methanol recovery was less than quantitative, possibly due to the formation of dimethylether. As in the prior example, large particle size 2,6-naphthalenedicarboxylic acid was produced, i.e., a median particle size of 188.3 microns.

EXAMPLE 4

Table 4 lists the results of the hydrolysis of dimethyl-2,6-naphthalenedicarboxylate in the batch-mode using a stirred, 2 liter, 316 stainless steel pressure reactor. No hydrolysis catalyst was used. The reactor was charged with 200 grams of dimethyl-2,6-naphthalenedicarboxylate and 1000 grams of distilled water. In each of Runs 1–3, the product 2,6-naphthalenedicarboxylic acid was separated from the remaining water, dried and analyzed.

During Runs 2 and 3, a portion of the gas phase of the reaction mixture was vented to remove water and methanol hydrolysis product. For Run 2, 110 grams of a gaseous mixture of methanol and water were removed from the reaction 15 minutes after the reaction mixture reached the noted reaction temperature. In Run 3, the reactor was vented twice, once as soon as the reactor reached the noted reaction temperature, and a second time 20 minutes later. In the first venting, 99 grams of a gaseous mixture of water and methanol were removed. In the second venting, 155 grams were removed. For Run 4, the reaction mixture was vented three times. Once when the reaction mixture reached the reaction temperature, then two more times at 10 minute intervals.

The solid reaction product comprising mainly 2,6-naphthalenedicarboxylic acid was, washed, as noted, by slurrying the product with three parts by weight of water for 30 minutes followed by filtration.

These data demonstrate that the hydrolysis reaction is rapid at 600° F. and that the venting of the reactor reduces the amount of MM-2,6-NDC and DM-2,6-NDC in the product.

TABLE 3

|  | Run 1 | Run 2 | Run 3 |
|---|---|---|---|
| Solvent Ratio[a] | 4:1 | 4:1 | 4:1 |
| Catalyst | None | None | None |
| Reaction Temp., °F. | 587 | 588 | 537 |
| Reaction Press., psig | 1410 | 1420 | 970 |
| Reaction Time, hrs. | 1.0 | 0.25 | 1.0 |
| Product Analysis |  |  |  |
| Visual Color | Gray | Off-White | Off-White |
| OD (380 nm) | 0.05 | 0.01 | 0.05 |
| Median Particle Size (Microns) | 188.3 |  |  |
| Mean Particle Size (Microns) | 214.8 |  |  |
| Wt. % DM-2,6-NDC | 0.29 | 0.496 | 0.329 |
| Wt. % MM-2,6-NDC | 3.75 | 4.89 | 2.95 |
| Recovered Methanol[b] | 51.6 | 74.7 | 86.8 |
| Metal Analysis,[c] ppm |  |  |  |
| Al | 5.9 | 3.19 | 10.3 |
| Ca | 3.7 |  | 6.5 |
| Fe | 2.27 | 2.79 | 2.27 |
| K |  | 1.8 | 2.1 |
| Mg |  |  | 1.79 |
| Ni | 1.2 |  | 1.46 |
| Ti | 7.6 | 14.6 | 16.6 |
| Zr |  | 3.49 | 4.1 |

[a]Weight ratio of water to DM-2,6-NDC
[b]% of theoretical
[c]Only for metals greater than 1 ppm

TABLE 4

|  | Run 1 | Run 2 |  | Run 3 | Run 4 |
|---|---|---|---|---|---|
| Solvent Ratio[a] | 5:1 | 10:1 |  | 10:1 | 10:1 |
| Catalyst | None | None |  | None | None |
| Reaction Temp., °F. | 600 | 600 |  | 600 | 600 |
| Reaction Time,[b] hrs. | 0.25 | 0.5 |  | 0.5 | 0.5 |
| Times vented | 0 | 1 |  | 2 | 3 |
| Filter Cake Washed | No | No | Yes | No | Yes | No |
| Product Analysis |  |  |  |  |  |
| Wt. % DM-2,6-NDC | 0.28 | 0.10 | 0.16 | 0.09 | 0.04 | 0.04 |
| Wt. % MM-2,6-NDC | 2.9 | 1.4 | 1.4 | 0.63 | 0.71 | 0.86 |
| Wt. % 2-NA | 0.19 | 0.34 | 0.18 | 0.05 | 0.05 | 0.41 |
| Visual Color | cream | — | — | — | — | beige |

[a]Weight ratio of water to DM-2,6-NDC
[b]Time at 600° F.

EXAMPLE 5

The hydrolysis of dimethyl-2,6-naphthalenedicarboxylate was conducted in the batch-mode in a 2 liter, stirred, titanium-lined reactor. The reaction time, temperature, pressure and analysis of the resulting 2,6-naphthalenedicarboxylic acid are provided in Table 5.

In Run 1, the reactor was charged with 150 grams of dimethyl-2,6-naphthalenedicarboxylate and 1500 grams of distilled water. When the reaction mixture reached 600° F., 75 grams of the gaseous mixture of water and methanol were vented from the reactor. This venting was repeated 20 minutes later. After a total reaction time of 30 minutes, the reaction mixture was cooled and, at a temperature of 309° F., the mother liquor was removed through a filter located at the bottom of the reactor. At this point, while the reactor was still at about 309° F., 300 grams of fresh distilled water were added to the reactor and the resulting slurry was stirred for about 15 minutes. The slurry was again filtered and the 2,6-naphthalenedicarboxylic acid product was dried and analyzed.

Run 2 was conducted in substantially the same manner except that 175 grams of dimethyl-2,6-naphthalenedicarboxylate were used, approximately 150 grams of the gaseous mixture of methanol and water were vented during each venting, the mother liquor was separated from the 2,6-naphthalenedicarboxylic acid product at 331° F., and the product was washed using 500 grams of distilled water at a temperature of about 250° F.

These data demonstrate that product of good color and low levels of DM-2,6-NDC and MM-2,6-NDC can be obtained using the process of this invention. The hot filtration appears to have reduced the level of 2-NA in the product relative to the results reported in Table 4. Additionally, the product filtered at the higher temperature exhibited superior color.

TABLE 5

|  | Run 1 | Run 2 |
|---|---|---|
| Solvent Ratio[a] | 10:1 | 10:1 |
| Catalyst | None | None |
| Reaction Temp., °F. | 600 | 600 |
| Reaction Time,[b] hrs. | 0.5 | 0.5 |
| Times Vented | 2 | 2 |
| Filtration Temperature; °F. | 309 | 331 |
| Product Analysis |  |  |
| Wt. % DM-2,6-NDC | 0.06 | 0.09 |
| Wt. % MM-2,6-NDC | 0.07 | 0.23 |
| Wt. % 2-NA | Not detected | Not detected |
| Visual Color | Off-white | White |
| Tri-stimulus Color |  |  |
| L | 91.27 | 94.85 |
| a* | −0.03 | −0.71 |
| b* | 4.97 | 3.7 |

[a]Weight ratio of water to DM-2,6-NDC
[b]Time at 600°F.

EXAMPLE 6

Dimethyl-2,6-naphthalenedicarboxylate was hydrolyzed in a 25 gallon, 316 stainless steel reactor in two separate runs according to the following procedure:

In Run 1, the reactor was charged with 23.9 lbs of dimethyl-2,6-naphthalenedicarboxylate and 110 lbs of distilled water. After 0.5 hours at the reaction temperature, the reactor was cooled to 258° F. and the product 2,6-naphthalenedicarboxylic acid was filtered from the water. The filter cake was washed with 25 lbs of near-boiling distilled water, and the product was dried and analyzed.

In Run 2, the reactor was charged with 25 lbs of dimethyl-2,6-naphthalenedicarboxylate and 110 lbs of water. The reaction mixture was maintained at the reaction temperature for 20 minutes and then cooled to 265° F. for filtration. The filter cake was washed with 50 lbs of hot distilled water before it was dried and analyzed.

Except for MM-2,6-NDC and DM-2,6-NDC, the products from these reactions contained 0.03 and 0.043 weight percent 2-NA, respectively, as the only significant impurity. Additionally, metals analysis of the product from Run 2 demonstrated a low level of metal contamination indicating that reactor corrosion was not significant.

The data for the two runs are summarized in Table 6.

TABLE 6

|  | Run 1 | Run 2 |
|---|---|---|
| Solvent Ratio[a] | 4.6 | 4.4 |
| Catalyst | None | None |
| Reaction Temp., °F. | 595–605 | 600–605 |
| Reaction Time, hrs. | 0.5 | 0.33 |
| Times Vented | None | None |
| Filtration Temp., °F. | 258 | 256 |
| Washed | Yes | Yes |
| Product Analysis |  |  |
| Wt. % DM-2,6-NDC | 1.2 | 2.9 |
| Wt. % MM-2,6-NDC | 1.9 | 4.8 |
| Wt. % 2-NA | 0.03 | 0.043 |
| Visual Color | Yellow | Yellow |
| Metals Analyses,[b] ppm |  |  |
| Na | ND | 1.4 |
| Fe | 2.5 |  |
| Al | 1.4 |  |
| Cr | 7.8 | 0.8 |

[a]Weight ratio of water to DM-2,6-NDC
[b]Only for metals greater than 1 ppm.

EXAMPLE 7

The hydrolysis of dimethyl-2,6-naphthalenedicarboxylate was conducted in a 300 ml, stirred, 316 stainless steel reactor fitted with a sample port for venting overhead vapor and a dip-leg sample tube for sampling the bottom, liquid phase of the reaction mixture. A mixture of 100 grams of distilled water and 20 grams of dimethyl-2,6-naphthalenedicarboxylate were used for each run. A hydrolysis catalyst was not added.

The reaction conditions and sample analysis data for three runs are reported in Table 7. Samples designated "1" were taken from the reaction bottom during the reaction. Samples designated as "D" are vapor samples taken at the reaction times indicated. At the end of the reaction, the reactor was rapidly cooled and the remaining liquid was removed by low-temperature distillation. Samples of the resulting liquid are designated "F". Finally, samples designated as "2" were taken from the dried and well-mixed reactor bottoms.

Run 1 was conducted at 625° F. The data from Run 1 indicates that most of the hydrolysis reaction occurs after only 15 minutes. A small amount of 2-NA was formed. No methanol was removed during the run.

Run 2 was conducted at 550° F. Again, high conversion was obtained after only 15 minutes (Sample 2, Run 2). However, in this run some vapor was removed from the reaction mixture (Sample D, Run 2). This sample contained 8.6 percent methanol (by weight) and about 17 grams of total material was removed. After 38 minutes of reaction time the reaction was terminated and the analysis of the product (Sample 2, Run 2) indicated 98.7 percent ester conversion (conversion of ester groups to acid groups). The final vapor sample (Sample F, Run 2) contained only 3 percent methanol compared to 5.4 percent in the sample from the previous run (Sample F, Run 1). This indicates that the removal of methanol during the run provided higher conversion of dimethyl-2,6-naphthalenedicarboxylate compared to Run 1 in Table 7, even at a lower reaction temperature.

Run 3 in Table 7 was conducted at 500° F. with vapor removal during the run. In this example, 42.7 percent conversion (conversion of ester groups to acid groups) was achieved after 15 minutes (Sample 1, Run 3). After vapor removal (Sample D, Run 3), the reaction was terminated at a total of 43 minutes reaction time. The conversion was 91.8 percent (conversion of ester groups to acid groups). Run 3 in Table 7 demonstrates that, as expected, the reaction rate decreases as the reaction temperature is decreased. However, the reaction was still rapid at 500° F. The Microtrac™ median particle size for the 2,6-NDA produced in Run 3 was 140 microns and the average particle size was 195 microns.

TABLE 7

| | Run 1 | | | Run 2 | | | | Run 3 | | |
|---|---|---|---|---|---|---|---|---|---|---|
| Solvent Ratio[a] | 5:1 | | | 5:1 | | | | 5:1 | | |
| Catalyst | None | | | None | | | | None | | |
| Reaction Temp., °F. | 625 | | | 550 | | | | 500 | | |
| Sample | 1 | 2 | F | 1 | D | 2 | F | 1 | D | 2 |
| Sample Location | Bottom | Bottom | Vapor | Bottom | Vapor | Bottom | Vapor | Bottom | Vapor | Bottom |
| Sample Time, min. | 15 | 30 | 30[b] | 15 | 15–22 | 38 | 38[b] | 15 | 16–24 | 43 |
| Sample Weight, g (wet) | | | | | | | | 4.5 | 24.56 | |
| Sample Weight, g (dry) | 0.98 | 15.9 | — | 0.6 | 0.05 | 16.4 | | 0.937 | 0.078 | 16.01 |
| Product Composition | | | | | | | | | | |
| Vapor, wt %: | | | | | | | | | | |
| MeOH | | | 5.4 | | 8.61 | | 3 | | 7.23 | |
| DME | | | 0.35 | | 0.22 | | 0 | | 0.054 | |
| Reactor Bottom. Wt. % | | | | | | | | | | |
| (after drying) | | | | | | | | | | |
| 2,6-NDA | 80.03 | 54.35 | | 67.3 | | 94.78 | | 17.28 | | 83.44 |
| DM-2,6-NDC | 0.55 | 0.33 | | 1.72 | | 0.14 | | 33.55 | | 2.27 |
| MN-2,6-NDC | 15.60 | 12.30 | | 25.21 | | 2.48 | | 40.30 | | 12.77 |
| 2-NA | 0.35 | 0.70 | | 0.00 | | 0.00 | | 0.00 | | 0.00 |
| Others | 0.07 | 0.17 | | 0.15 | | 0.06 | | 0.20 | | 0.11 |
| Totals | 96.60 | 97.85 | | 94.81 | | 97.46 | | 91.33 | | 98.59 |
| Reactor Bottom, mole % | | | | | | | | | | |
| 2,6-NDA | 84.1 | 87.7 | | 72.9 | | 97.5 | | 20.4 | | 85.6 |
| DM-2,6-NDC | 0.5 | 0.3 | | 1.6 | | 0.1 | | 35.0 | | 2.1 |
| MM-2,6-NDC | 15.4 | 12.0 | | 25.5 | | 2.4 | | 44.6 | | 12.3 |
| Total Mole % Ester Groups | 8.2 | 6.3 | | 14.4 | | 1.3 | | 57.3 | | 8.2 |
| Total Mole % Acid Groups | 91.8 | 93.7 | | 85.6 | | 98.7 | | 42.7 | | 91.8 |

[a]Weight ratio of water to DM-2,6-NDC charged to reactor.
[b]At end of reaction.

EXAMPLE 8

This example reports the crystal morphology for 2,6-naphthalenedicarboxylic acid produced by the hydrolysis process of this invention as well as by a low-temperature hydrolysis process such as that reported in Example 1. The morphology was determined by scanning electron microscopy analysis.

| Hydrolysis Process | 2B-NDA Particle Morphology |
|---|---|
| Low-temperature hydrolysis catalyzed by p-toluene sulfonic acid. 5:1 weight ratio of water to DM-2,6-NDC. Reaction temperature of 390–400° F.. | Particles up to about 60 microns at low magnification. At high magnification, particles appear as highly porous agglomerates of small crystals wherein the small crystals have a length of about 1 micron and a width of a few tenths of a micron. |
| High-temperature hydrolysis. No catalyst. 4:1 weight ratio of water to DM-2,6-NDC. Reaction temperature 587° F.. 2,6-NDA prepared by Example 3, Run 1. | Particles are well-formed, substantially non-porous crystals with a median particle size of greater than 100 microns as measured by the Microtrac ™ particle analyzer. |
| High-temperature hydrolysis. No catalyst. 4:1 weight ratio of water to DM-2,6-NDC. Reaction temperature of 537° F.. 2,6-NDA prepared by Example 3, Run 3. | Particles typically greater than 100 microns in length, consisting of agglomerates of smaller crystals having a length of about 20–50 microns and a width of about 5–10 microns. |

EXAMPLE 9

This example reports the results of a qualitative analyses conducted to determine the amount of ethylene glycol that is required to form pumpable slurries of 2,6-naphthalenedicarboxylic acid in ethylene glycol.

Reported below are the minimum grams of ethylene glycol per gram of 2,6-naphthalenedicarboxylic acid that are required to form a "paste" and a "slurry". "Paste" is defined as a mixture with all the crystals wetted. "Slurry" is defined as a mixture that has a smooth, creamy consistency

| Hydrolysis Process | Paste | Slurry |
|---|---|---|
| 2,6-NDA produced by low-temperature process as reported in Example 1. | 0.802 | 0.966 |
| Process of this invention as reported in Example 3, Run 1. | 0.513 | 0.666 |

Although these data are qualitative, they demonstrate that the 2,6-naphthalenedicarboxylic acid produced by the low-temperature process requires approximately 50% more ethylene glycol to produce a slurry compared to the 2,6-NDA produced at 590° F.

EXAMPLE 10

Table 8 reports the Brookfield viscosities of mixtures of ethylene glycol and 2,6-naphthalenedicarboxylic acid. These data demonstrate that the 2,6-naphthalenedicarboxylic acid prepared in Example 6 according to the hydrolysis process of this invention provides for a substantially less viscous mixture of 2,6-naphthalenedicarboxylic acid and ethylene glycol compared to the 2,6-naphthalenedicarboxylic acid prepared by a low-temperature process as exemplified by Example 1.

TABLE 8

| Mole Ratio Ethylene Glycol: 2,6-NDA | Brookfield Viscosity[a] | |
|---|---|---|
| | 2,6-NDA (Example 6) | 2,6-NDA Low-Temp. Process[b] |
| 2.0 | 12,373 | |
| 2.5 | 2,480 | |
| 3.0 | 800 | |
| 3.5 | 373 | 20,160 |
| 4.0 | | 10,293 |
| 4.5 | | 6,240 |
| 5.0 | | 4,320 |
| 5.5 | | 3,253 |
| 6.0 | | 2,400 |
| 6.5 | | 1,760 |
| 7.0 | | 1,280 |
| 7.5 | | 1,120 |
| 8.0 | | 960 |
| 8.5 | | 800 |

[a]Viscosities in centipoise measured using a #4 spindle at room temperature (ca 70° F.) and at 50 rpm.
[b]Prepared by process equivalent to that reported in Example 1 using a reaction temperature of 380–400° F. and a weight ratio of water to DM-2,6-NDC of 5:1.

EXAMPLE 11

Solubility data for 2,6-naphthalenedicarboxylic acid in distilled water and acetic acid is listed below. These data can be used to calculate the percent 2,6-NDA solubilized in water or acetic acid at the listed reaction temperature.

| Temperature (C/°F.) | Solubility (grams 2,6-NDA/100 g Solvent) | | |
|---|---|---|---|
| | Water | Acetic Acid | Acetic Acid Water* |
| 160/320 | 0.041 | 0.16 | 0.18 |
| 200/392 | 0.22 | 0.44 | 0.59 |
| 240/464 | 1.19 | 1.2 | 2.0 |
| 280/536 | 6.07 | 3.1 | 4.5 |
| 320/608 | 33.2 | | 10.8 |

*85 wt. % acetic acid and 15 wt. % water.

Plots of this data as the Ln(grams 2,6-NDN100 grams solvent) vs. temperature are linear and, therefore, provides for other solubility values by interpolation or extrapolation.

EXAMPLE 12

The following is the general procedure for Runs 1–7 in Table 9

A 50 ml pressure vessel, fitted with an internal thermocouple and mounted in an external shaker, was charged with the indicated amount of 2,6-NDA and distilled water. The 2,6-NDA was crude 2,6-NDA prepared by the cobalt, manganese, bromine catalyzed liquid-phase oxidation of 2,6-dimethylnaphthalene, and contained the metal and organic impurities listed in Table 9. After purging the reactor with helium to remove oxygen, the reactor was sealed and the contents were mixed by shaking at 360 cycles/minute (cpm). While shaking at this speed, the reactor was immersed into a heated, fluidized sand bath to obtain the indicated internal temperature within 3 minutes. After maintaining the indicated temperature for the residence time listed, the reactor was withdrawn from the sand bath and allowed to cool while maintaining the shaking. The rate of cooling was adjusted by the amount of cooling air directed on the exterior of the reactor.

Following the reaction and cooling, the reactor was weighed to determine the amount of weight change due to leaking (see "Product Weight" in Table 9). The product was removed from the reactor at ambient temperature using cold distilled water to facilitate the transfer. The mixture was filtered and both cake and filtrate were dried in a vacuum oven at 85° C. for 4–8 hours. The dried product weight was obtained ("Dry Down Weight") by summing the weights of the dried cake and filtrate. In all cases, the mass-balance exceeded 95% and in most cases exceeded 98% of the initial charge.

The solid from both the filtrate and cake were analyzed by liquid chromatography. Table 9 reports the calculated total product by combining the weights of each component in the cake and the dried filtrate. The liquid chromatography results are most accurate for the impurities while the 2,6-NDA weight percent ["2,6-NDA (Detected)" in the tables] is generally a less accurate measure due to the magnitude of the signal from the liquid chromatography detector. Partial correction is obtained by normalizing the 2,6-NDA value by dividing 2,6-NDA detected by the total weight % detected and multiplying by 100 to give "2,6 NDA (% of Total)" values in the table. In no case was there evidence of decomposition of 2,6-NDA exceeding about 1 weight %. The particle size was measured by Microtrac™ analyzer as previously described.

Runs 1–3 in Table 9 were conducted using the identical 2,6-NDA feedstock, temperature and residence time but with different cooling rates. All three runs demonstrate a TMLA conversion above 69% and a Br-2,6-NDA conversion of above 56%, while 2,6-NDA formation was less than 0.2%. The slower cooling rates gave higher conversions of impurities.

The slower cooling rate also resulted in increased particle size from a mean of 54 microns at the fastest cooling rate of 125° F./minute to a mean of 207 microns at 6.5° F./minute. At all cooling rates, the percent of particles less than 11 microns ("fines") was drastically reduced from 40% in the 2,6-NDA feedstock to less than 3% in the product. This reduction in fines will greatly improve the performance of whatever solid/liquid separation device is used to separate the purified 2,6-naphthalene dicarboxylic acid from the reaction mixture mother liquor.

Runs 1–3 in Table 9 demonstrates that slower cooling is desirable to obtain high impurity conversion and largest particle size. These runs also demonstrate the unexpected feature of this invention wherein the TMLA and Br-2,6-NDA are convened during the heating step of this invention.

Runs 4–6 in Table 9 were conducted at conditions similar to Runs 1–3 except that the reaction temperature was varied from 600° F. in Run 4 to 540° F. in Run 6. The result of the reduced temperature was that both impurity conversion and particle size decreased. At the lower temperature of 540° F., the mean particle size was 38 microns compared to 21.7 microns in the feedstock, and the percent of fines that were less than 11 microns was 18%. While both of these values show an improvement over the 2,6-NDA feedstock, they indicate that purification was not complete in the 10 minute reaction time. A longer reaction time would be expected to improve the results at 540° F. The results at 540° F. indicate that a preferred temperature is at least about 550° F.

In Run 7, in Table 9, less water and more crude 2,6-NDA was used to increase the solvent/solids ratio from 5:1 (16.7% solids) to 4:1 (20.0% solids). Heating at 600° F. with the moderate cooling rate similar to that used in Run 4 yielded product similar to that obtained in Run 4 with high Br-2,6-

NDA conversion, moderate TMLA conversion, and less than 0.2% formation of 2-NA.

EXAMPLE 13

Run 8 in Table 10 was conducted to determine the degree of impurity formation during the high temperature treatment of a 2,6-NDA feedstock containing no metals and few organic impurities. In this run, which used the same reactor as used for Runs 1–7 in Example 12, purified 2,6-NDA was used. The pure 2,6-NDA was obtained by hydrolysis of the purified dimethyl ester of 2,6-NDA. The purified 2,6-NDA feed contained 1.4 weight % ester. The product from the high temperature treatment contained 0.3% of the esters and 0.5% of other unknowns, measured by liquid chromatography, indicating that decomposition of 2,6-NDA was low.

EXAMPLE 14

In Runs 9 and 10 in Table 11, the high temperature treatment of crude 2,6-NDA was conducted on a larger scale than in Runs 1–8 of Example 12 in order to allow hot filtration of the product at temperatures above the boiling point of water.

Run 9 was conducted in a 300 ml autoclave. The feed was crude 2,6-NDA in the form of a wet cake isolated from an oxidation reaction. This wet cake contained 20.2 g solids, 6 g acetic acid and 1 g water. To the wet cake was added 93 g water. Following the high temperature treatment at the specified conditions, the reactor was cooled to room temperature, opened and a sintered stainless steel filter on the end of a metal tube was placed in the bottom of the reactor. The reactor was again heated to 400° F. for 10 minutes then the liquid was allowed to flow out of the reactor through the filter. An additional 40 ml of water was added to the reactor and following 5 minutes of stirring, the filtrate was removed through the filter again. The cake and the combined flitrates were dried and analyzed yielding the data in Table 11.

The analyses for Run 9A–9C indicate that the high temperature treatment of 2,6-NDA in water followed by hot filtration yields a product with very little TMLA and 2-NA, an 88% reduction in the amount of Br-2,6-NDA, a 50% reduction in the 2-FNA, non-detectable amounts of Co and Mn metals, and an 84% reduction in total bromine. In addition, the particle size was increased by about 10 times and the fines smaller than 11 microns were eliminated.

About 74% of the TMLA originally present was converted to "other" components (mostly isophthalic acid and terephthalic acid) which are also mainly in the filtrate. This conversion of TMLA makes the mother liquor a potentially better material for recycle to the oxidation reactor where TMLA is known to be detrimental to oxidation catalyst activity. The 1.49 g of mother liquor solids contains only about 21% of 2,6-NDA, which is less than 2% of the 2,6-NDA in the feed used.

Run 10 was conducted in a one-gallon pressure reactor with an internal filter in the bottom of the reactor. The 5:1, by weight, mixture of water/crude 2,6-NDA was heated to 585° F. then cooled after 15 minutes. At 300° F., the filtrate was removed from the reactor, and an additional 400 g of water was reslurried with the cake at 300° F. and removed by filtration. This lower temperature treatment removed from the crude 2,6-NDA 69% of the Co and 56% of the Mn. TMLA, Br-2,6-NDA and 2-NA were not detected. The particle size of the 2,6-NDA increased by over 10 times from a mean of 21 microns to 316 microns. No fines less than 11 microns were detected in the product. The overall conversion of TMLA was 85%, and 99% of the Br-2,6-NDA was convened during the high temperature treatment. The mother liquor solids contained only 0.6% of the initial charge of 2,6-NDA.

EXAMPLE 15

A 300 ml Autoclave high pressure reactor equipped with a stirrer, internal thermocouple, pressure indicator, and inlet and outlet lines was charged with 100 grams water and 20.02 g impure 2,6-NDA (very fine powder with a light yellow color) with the analysis given in Table 12. In an aluminum screen basket was placed 2.07 of 0.5% palladium on carbon catalyst and the basket was fixed in the reactor above the stirrer but below the surface level of the liquid. After purging the reactor with helium to remove oxygen, the reactor was charged with 300 psig of hydrogen (at 72° F.). While stirring at a low rate, (250 rpm) the reactor was heated over 20 minutes to 600° F. and this temperature was maintained for 30 minutes. The reactor pressure was noted to be 1510 psig at 600° F. The reactor was then cooled from 600° F. to 400° F. over 35 minutes then from 400° F. to 77° F. over 70 minutes. At 77° F. the reactor pressure was 210 psig from the remaining hydrogen. The reactor was opened and a sample of the mixed solids was taken for analysis. It was observed that the solids in the reactor were of a white color with a slight greenish tint. Microscopic examination indicated that the sample of product was comprised of crystalline material with some crystals as large as 700 micron maximum length. Upon drying, the solid was off-white crystals with the analysis given in Table 12.

TABLE 9

| Run # | 2,6-NDA Feed* | 1 | 2 | 3 | 4 | 5 | 6 | 7 |
|---|---|---|---|---|---|---|---|---|
| Reactor Charge | | | | | | | | |
| 2,6-NDA (g) | | 5.00 | 5.00 | 5.00 | 5.00 | 5.00 | 5.00 | 6.00 |
| Water (g) | | 25.00 | 25.00 | 25.00 | 25.00 | 25.00 | 25.00 | 24.00 |
| Total (g) | | 30.00 | 30.00 | 30.00 | 30.00 | 30.00 | 30.00 | 30.00 |
| Reaction Conditions | | | | | | | | |
| Temperature (°F.) | | 630 | 630 | 630 | 600 | 570 | 540 | 600 |
| Time (min.) | | 10 | 10 | 10 | 10 | 10 | 10 | 10 |
| Cooling Rate (°F./min.) | | 125 | 16 | 6.5 | 16 | 17 | 18 | 16 |
| Shaking Speed (cpm) | | 360 | 360 | 360 | 360 | 360 | 360 | 360 |

TABLE 9-continued

| Run # | 2,6-NDA Feed[a] | 1 | 2 | 3 | 4 | 5 | 6 | 7 |
|---|---|---|---|---|---|---|---|---|
| Product Weight (g) | | 30.07 | 29.88 | 29.98 | 30.05 | 30.01 | 29.96 | 30.11 |
| Dry Down Weight (g) | | 4.77 | 4.88 | 4.91 | 4.94 | 4.91 | 4.92 | 5.92 |
| Product Analysis (Wt. %) | | | | | | | | |
| 2,6-NDA (Detected) | 93.25 | 93.49 | 93.02 | 93.41 | 86.76 | 93.56 | 87.76 | 94.16 |
| 2,6-NDA (% of Total) | 97.42 | 96.65 | 97.04 | 96.11 | 96.36 | 96.87 | 96.07 | 96.91 |
| 2,7-NDA | 0.01 | 0.00 | 0.00 | 0.00 | 0.00 | 0.00 | 0.00 | 0.00 |
| TMLA | 0.36 | 0.11 | 0.07 | 0.07 | 0.25 | 0.34 | 0.64 | 0.20 |
| Br-2,6-NDA | 0.55 | 0.24 | 0.16 | 0.06 | 0.01 | 0.20 | 0.38 | 0.04 |
| 2-FNA | 0.62 | 0.59 | 0.55 | 0.53 | 0.52 | 0.63 | 0.59 | 0.61 |
| 2-NA | 0.00 | 0.12 | 0.10 | 0.18 | 0.02 | 0.02 | 0.02 | 0.01 |
| Others | 0.93 | 2.18 | 1.96 | 2.94 | 2.48 | 1.83 | 1.95 | 2.04 |
| Total (Detected) | 95.72 | 96.73 | 95.85 | 97.19 | 90.06 | 96.59 | 91.35 | 97.16 |
| Metal Analysis (Wt. %) | | | | | | | | |
| Cobalt | 0.05 | | | | | | | |
| Manganese | 0.20 | | | | | | | |
| Bromine | 0.28 | | | | | | | |
| Particle Size | | | | | | | | |
| Mean (micron) | 21.7 | 54 | 133 | 207 | 230 | 126 | 38 | 254 |
| % < 11 microns | 40.1 | 2.2 | 0 | 0 | 0 | 2.3 | 18.1 | 0 |
| Relative % Conversion of Impurity | | | | | | | | |
| TMLA | | 69.5 | 79.7 | 81.0 | 28.6 | 5.2 | −81.6 | 43.1 |
| Br-2,6-NDA | | 55.9 | 71.7 | 88.3 | 99.0 | 62.8 | 30.2 | 92.5 |
| 2-FNA | | 4.1 | 10.8 | 14.7 | 16.4 | −1.6 | 5.0 | 0.8 |

[a]For Runs 1–7.

TABLE 10

| Run # | 2,6-NDA Feed | B |
|---|---|---|
| Reactor Charge | | |
| 2,6-NDA (g) | | 5.00 |
| Water (g) | | 25.00 |
| Total (g) | | 30.00 |
| Reaction Conditions | | |
| Temperature (°F.) | | 600 |
| Time (min.) | | 10 |
| Cooling Rate (°F./min) | | 17 |
| Shaking Speed (cpm) | | 360 |
| Product Weight (g) | | 30.02 |
| Dry Down Weight (g) | | 5.00 |
| Product Analysis (Wt. %) | | |
| 2,6-NDA (Detected) | 97.06 | 101.04 |
| 2,6-NDA (% of Total) | 98.13 | 98.40 |
| 2,7-NDA | 0.00 | 0.00 |
| TMLA | 0.00 | 0.00 |
| Br-2,6-NDA | 0.00 | 0.00 |
| 2-FNA | 0.00 | 0.00 |
| 2-NA | 0.00 | 0.52 |
| Others | 1.85 | 1.13 |
| Total (Detected) | 98.91 | 102.68 |
| Metal Analysis (Wt. %) | | |
| Cobalt | 0.00 | |
| Manganese | 0.00 | |
| Bromine | 0.00 | |

TABLE 11

| Run # | 2,6-NDA Feed | 9 | 2,6-NDA Feed | 10 |
|---|---|---|---|---|
| Reactor Charge | | | | |
| 2,6-NDA (g) | | 20.21 | | 200 |
| Water/Acetic Acid (g) | | 94/6 | | 1000/0 |
| Total (g) | | 120.21 | | 1200 |
| Reaction Conditions | | | | |
| Temperature (°F.) | | 600 | | 585 |
| Time (min.) | | 10 | | 15 |
| Cooling Rate (°F./min) | | 8.3 | | 4.9 |
| Stirring Speed (rpm) | | 250 | | 300 |

| | | 9 | | | | 10 | |
|---|---|---|---|---|---|---|---|
| Run # | 2,6-NDA Feed | 9A (Filtrate)$^c$ | 9B (Cake) | 9C (Combined Cake & filtrate) | 2,6-NDA Feed | 10A (Cake) | 10B (Filtrate) | 10C (Combined Cake & Filtrate) |
| Product Dry Down Weight (g) | | 1.49 | 18.03 | 19.52 | | 186.00 | 9.10 | 195.10 |
| Product Analysis (wt. %) | | | | | | | | |
| 2,6-NDA (Detected) | 91.69 | 21.21 | 97.80 | 91.96 | 90.06 | 93.54 | 11.52 | 89.71 |
| 2,6-NDA (% of Total) | 95.67 | 29.13 | 98.99 | 94.99 | 95.86 | 99.37 | 13.41 | 95.69 |
| 2,7-NDA | 0.01 | 0.24 | 0.00 | 0.02 | 0.01 | 0.00 | 0.40 | 0.02 |
| TMLA* | 2.44 | 8.40 | ND | 0.64 | 2.19 | ND | 7.14 | 0.33 |
| Br-2,6-NDA | 0.58 | 0.50 | 0.07 | 0.10 | 0.59 | 0.00 | 0.11 | 0.01 |
| 2-FNA | 0.30 | 1.65 | 0.15 | 0.27 | 0.30 | 0.19 | 2.14 | 0.28 |
| 2-NA | 0.08 | 2.58 | 0.00 | 0.20 | 0.00 | 0.00 | 4.08 | 0.19 |
| Others | 0.74 | 38.24 | 0.77 | 3.63 | 0.81 | 0.40 | 60.54 | 3.21 |
| Total (Detected) | 95.84 | 72.93 | 98.19 | 96.81 | 93.95 | 94.14 | 85.93 | 93.75 |
| Metal Analysis (wt. %) | | | | | | | | |
| Cobalt | 0.12 | 1.19 | 0.00 | 0.09 | 0.13 | 0.03 | 2.52 | 0.15 |
| Manganese | 0.75 | 7.60 | 0.00 | 0.58 | 0.75 | 0.30 | 13.50 | 0.92 |
| Bromine | 0.38 | 3.75 | 0.06 | 0.34 | 0.37 | 0.01 | 15.00 | 0.71 |
| Particle Size | | | | | | | | |
| Mean (microns) | 24 | | 235 | | 21 | 316 | | |
| % < 11 microns | 19.9 | | 0.00 | | 24 | 0.00 | | |
| Relative % Conversion of Impurities | | | | | | | | |
| TMLA | | | | 73.8 | | | | 84.8 |
| Br-216-NDA | | | | 82.6 | | | | 99.1 |
| 2-FNA | | | | 9.6 | | | | 4.8 |

*These values are +/−0.1

This example demonstrates that both the Br-2,6-NDA and the 2-FNA can be substantially converted without significant decarboxylation of the 2,6-NDA to 2-naphthoic acid. The treatment also readily removed the TMLA from the crystals even though no washing of the crystals was conducted. Finally, a reduction in color intensity was a positive indication that other high molecular weight impurities are being converted by the process.

TABLE 12

| Composition by | Weight % | |
|---|---|---|
| Liquid Chromatography | Crude 2,6-NDA | Example |
| TMLA* | 0.355 | 0.00 |
| 2,6-NDA | 93.252 | 93.689 |
| Br-2,6-NDA | 0.548 | 0.00 |
| 2-FNA | 0.619 | 0.00 |
| 2-NA | 0.000 | 0.176 |
| Other Unknowns | 0.932 | 0.419 |
| Total | 95.715 | 94.284 |

*Values are +/− 0.1

While only certain embodiments of the present invention have been set forth, alternative embodiments and various modifications will be apparent from the above description to those skilled in the art. These and other alternatives are considered equivalents, and are within the spirit and scope of the present invention.

That which is claimed is:

1. A process for preparing purified 2,6-naphthalenedicarboxylic acid comprising:
    a) hydrolyzing a dialkyl-2,6-naphthalenedicarboxylate with water at a reaction temperature of at least about 450° F. under liquid phase conditions and for a time sufficient to convert a major portion of the dialkyl-2,6-naphthalenedicarboxylate to 2,6-naphthalenedicarboxylic acid thereby forming a reaction product mixture, the amount of water present being sufficient to solubilize, at the reaction temperature, at least about 10 weight percent of the 2,6-naphthalenedicarboxylic acid formed; and
    b) recovering 2,6-naphthalenedicarboxylic acid from the reaction product mixture.

2. The process of claim 1 wherein the amount of water present is an amount sufficient to solubilize at least about 50 weight percent of the 2,6-naphthalenedicarboxylic acid present in the reaction product mixture.

3. The process of claim 1 wherein the amount of water present is an amount sufficient to solubilize substantially all of the 2,6-naphthalenedicarboxylic acid present in the reaction product mixture.

4. The process of claim 1 wherein at least about 95 weight percent of the dialkyl-2,6-naphthalenedicarboxylate is converted to 2,6-naphthalenedicarboxylic acid.

5. The process of claim 1 wherein the reaction temperature is at least about 540° F.

6. The process of claim 1 wherein the reaction temperature is at least about 570° F.

7. The process of claim 1 wherein the alkyl portion of the dialkyl-2,6-naphthalenedicarboxylate contains 1 to about 4 carbon atoms.

8. The process of claim 1 wherein the dialkyl-2,6-naphthalenedicarboxylate is dimethyl-2,6-naphthalenedicarboxylate.

9. The process of claim 8 wherein the dimethyl-2,6-naphthalenedicarboxylate is at least about 98% pure.

10. The process of claim 1 wherein the 2,6-naphthalenedicarboxylic acid formed has an average particle size of at least about 100 microns.

11. The process of claim 3 wherein the reaction temperature is at least about 570° F. and wherein at least about 95 weight percent of the alkyl-2,6-naphthalenedicarboxylate is converted to 2,6-naphthalenedicarboxylic acid.

12. The process of claim 11 wherein the 2,6-naphthalenedicarboxylic acid product is in the form of crystals, the crystals having an average size of at least about 100 microns.

13. The process of claim 1 wherein the reaction temperature is at least about 540° F., the dialkyl-2,6-naphthalenedicarboxylate is dimethyl-2,6-naphthalenedicarboxylate and wherein the weight ratio of water to dimethyl-2,6-naphthalenedicarboxylate is at least about 4:1, respectively.

14. The process of claim 13 wherein the reaction temperature is at least about 570° F.

15. The process of claim 14 wherein a column reactor is used as a reaction zone.

16. The process of claim 15 wherein the column reactor contains a plurality of trays to provide for liquid hold up.

* * * * *